US010662249B1

(12) United States Patent
Hu et al.

(10) Patent No.: US 10,662,249 B1
(45) Date of Patent: May 26, 2020

(54) ANTIBODIES TARGETING CD40 AND USES THEREOF

(71) Applicants: Beijing Mabworks Biotech Co., Ltd., Beijing (CN); Beijing Mabridge Biopharmaceutical Co., Ltd, Beijing (CN)

(72) Inventors: Wenqi Hu, Las Vegas, NV (US); Jiangmei Li, Beijing (CN); Feng Li, Beijing (CN)

(73) Assignees: BEIJING MABWORKS BIOTECH CO., LTD., Beijing (CN); BEIJING MABRIDGE BIOPHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 16/726,160

(22) Filed: Dec. 23, 2019

Related U.S. Application Data

(62) Division of application No. 16/290,980, filed on Mar. 4, 2019.

(51) Int. Cl.
| | |
|---|---|
| *C07K 16/00* | (2006.01) |
| *C07K 16/28* | (2006.01) |
| *C07K 16/46* | (2006.01) |
| *A61K 39/395* | (2006.01) |
| *A61K 31/282* | (2006.01) |
| *A61K 31/704* | (2006.01) |
| *A61P 35/00* | (2006.01) |
| *A61K 38/20* | (2006.01) |
| *A61K 38/19* | (2006.01) |

(52) U.S. Cl.
CPC ........ *C07K 16/2878* (2013.01); *A61K 31/282* (2013.01); *A61K 31/704* (2013.01); *A61K 38/193* (2013.01); *A61K 38/2026* (2013.01); *A61P 35/00* (2018.01); *C07K 16/2818* (2013.01); *C07K 16/2827* (2013.01)

(58) Field of Classification Search
None
See application file for complete search history.

(56) References Cited

U.S. PATENT DOCUMENTS

| 7,338,660 B2 | 3/2008 | Bedian et al. | |
| 10,570,210 B1 * | 2/2020 | Hu ..................... | A61K 38/2026 |
| 2014/0120103 A1 | 5/2014 | Zhang et al. | |
| 2016/0311916 A1 | 10/2016 | Ellmark | |

OTHER PUBLICATIONS

Angelou, Anastasios, et al. "The role of soluble CD40L ligand in human carcinogenesis." Anticancer Research 38.5 (2018): 3199-3201.

Ara, Anjuman, et al. "Multiple effects of CD40—CD40L axis in immunity against infection and cancer." ImmunoTargets and Therapy 7 (2018): 55-61.

Beatty, Gregory L., et al. "A phase I study of an agonist CD40 monoclonal antibody (CP-870,893) in combination with gemcitabine in patients with advanced pancreatic ductal adenocarcinoma." Clinical Cancer Research 19.22 (2013): 6286-6295.

Beatty, Gregory L., et al. "Cancer immunotherapy: activating innate and adaptive immunity through CD40 agonists." Expert Review of Anticancer Therapy 17.2 (2017): 175-186.

Bensinger, William, et al. "A phase I study of lucatumumab, a fully human anti-CD 40 antagonist monoclonal antibody administered intravenously to patients with relapsed or refractory multiple myeloma." British Journal of Haematology 159.1 (2012): 58-66.

Chowdhury, Ferdousi, et al. "Ex vivo assays of dendritic cell activation and cytokine profiles as predictors of in vivo effects in an anti-human CD40 monoclonal antibody ChiLob 7/4 phase I trial." Cancer Immunology Research 2.3 (2014): 229-240.

Costello, Régis T., et al. "What is the real role of CD40 in cancer immunotherapy?." Immunology Today 20.11 (1999): 488-493.

De Vos, Sven, et al. "A phase II study of dacetuzumab (SGN-40) in patients with relapsed diffuse large B-cell lymphoma (DLBCL) and correlative analyses of patient-specific factors." Journal of Hematology & Oncology 7.1 (2014): 44, 9 pages.

Gladue, Ronald P., et al. "The CD40 agonist antibody CP-870,893 enhances dendritic cell and B-cell activity and promotes anti-tumor efficacy in SCID-hu mice." Cancer Immunology, Immunotherapy 60.7 (2011): 1009-1017.

Hussein, Mohamad, et al. "A phase I multidose study of dacetuzumab (SGN-40; humanized anti-CD40 monoclonal antibody) in patients with multiple myeloma." Haematologica 95.5 (2010): 845-848.

Kornbluth, Richard S., et al. "Design of CD40 agonists and their use in growing B cells for cancer immunotherapy." International Reviews of Immunology 31.4 (2012): 279-288.

Lapalombella, Rosa, et al. "The humanized CD40 antibody SGN-40 demonstrates pre-clinical activity that is enhanced by lenalidomide in chronic lymphocytic leukaemia." British Journal of Haematology 144.6 (2009): 848-855.

Lee, Ho H., et al. "NF-κB-mediated up-regulation of Bcl-x and Bfl-1/A1 is required for CD40 survival signaling in B lymphocytes." Proceedings of the National Academy of Sciences 96.16 (1999): 9136-9141.

Luqman, Mohammad, et al. "The antileukemia activity of a human anti-CD40 antagonist antibody, HCD122, on human chronic lymphocytic leukemia cells." Blood, The Journal of the American Society of Hematology 112.3 (2008): 711-720.

(Continued)

*Primary Examiner* — Maher M Haddad
(74) *Attorney, Agent, or Firm* — Duane Morris LLP; Thomas J. Kowalski; Deborah L. Lu

(57) ABSTRACT

An isolated monoclonal antibody that specifically binds human CD40. A nucleic acid molecule encoding the antibody, an expression vector, a host cell and a method for expressing the antibody are also provided. The present invention further provides an immunoconjugate, a bispecific molecule, a chimeric antigen receptor, an oncolytic virus and a pharmaceutical composition comprising the antibody, as well as a treatment method using an anti-CD40 antibody of the invention.

17 Claims, 12 Drawing Sheets

Specification includes a Sequence Listing.

(56) References Cited

OTHER PUBLICATIONS

Moran, Amy E., et al. "The TNFRs OX40, 4-1BB, and CD40 as targets for cancer immunotherapy." Current Opinion in Immunology 25.2 (2013): 230-237.

Nowak, A. K., et al. "A phase 1b clinical trial of the CD40-activating antibody CP-870,893 in combination with cisplatin and pemetrexed in malignant pleural mesothelioma." *Annals of Oncology* 26.12 (2015): 2483-2490.

Schultze, Joachim L., et al. "DCs and CD40-activated B cells: current and future avenues to cellular cancer immunotherapy." Trends in Immunology 25.12 (2004): 659-664.

Tong, Alex W., and Marvin J. Stone. "Prospects for CD40-directed experimental therapy of human cancer." Cancer Gene Therapy 10.1 (2003): 1-13.

Vonderheide, Robert H., et al. "Clinical activity and immune modulation in cancer patients treated with CP-870,893, a novel CD40 agonist monoclonal antibody." Journal of Clinical Oncology 25.7 (2007): 876-883.

Vonderheide, Robert H., et al. "Phase I study of the CD40 agonist antibody CP-870,893 combined with carboplatin and paclitaxel in patients with advanced solid tumors." Oncoimmunology 2.1 (2013): e23033, 10 pages.

Brown, McKay, et al. "Tolerance of single, but not multiple, amino acid replacements in antibody VH CDR 2: a means of minimizing B cell wastage from somatic hypermutation?." The Journal of Immunology 156.9 (1996): 3285-3291.

Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.

Paul, Fundamental Immunology, 3rd Edition, (1993) pp. 292-295.

Rudikoff, Stuart, et al. "Single amino acid substitution altering antigen-binding specificity." Proceedings of the National Academy of Sciences 79.6 (1982): 1979-1983.

Dahan, Rony, et al. "Therapeutic activity of agonistic, human anti-CD40 monoclonal antibodies requires selective FcγR engagement." Cancer Cell 29.6 (2016): 820-831.

\* cited by examiner

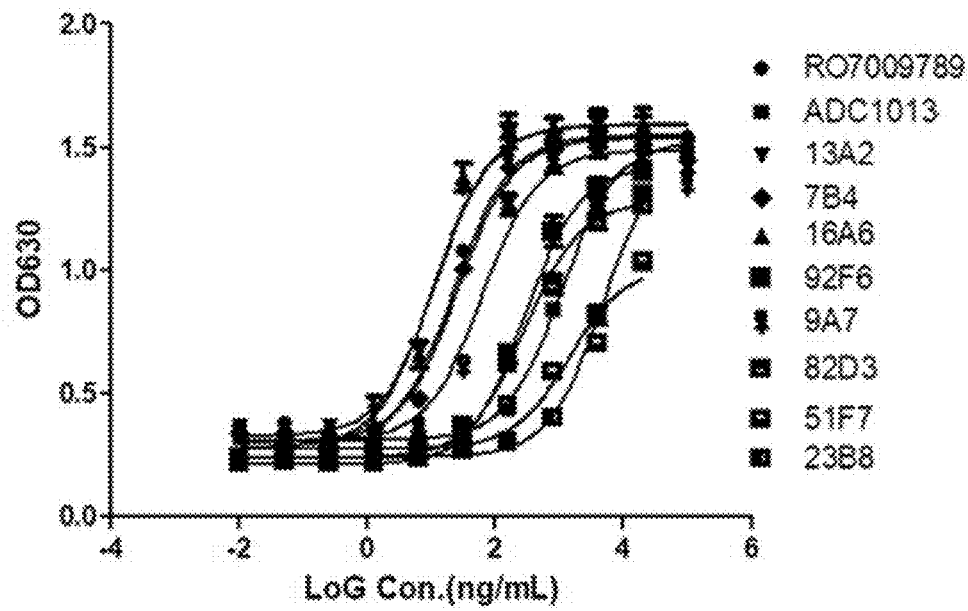
FIG. 3
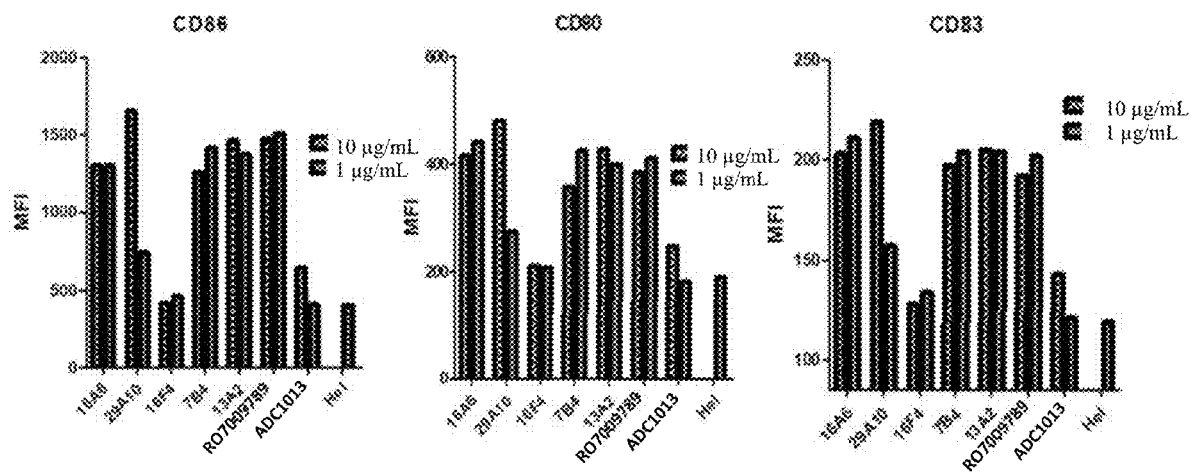
FIG. 4A          FIG. 4B          FIG. 4C

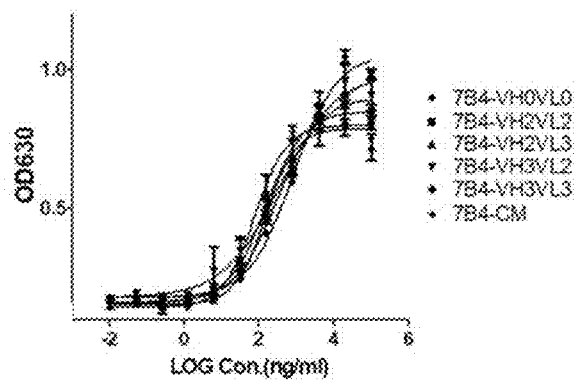
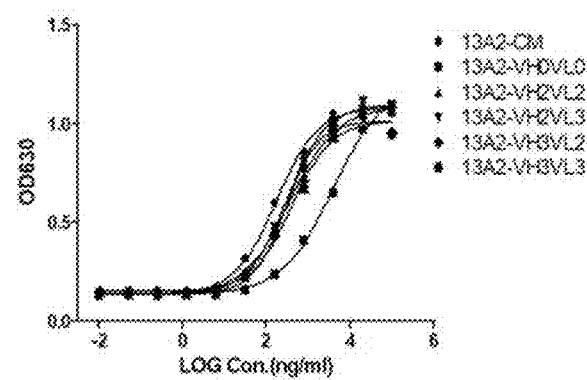
FIG. 9A　　　　　　　FIG. 9B
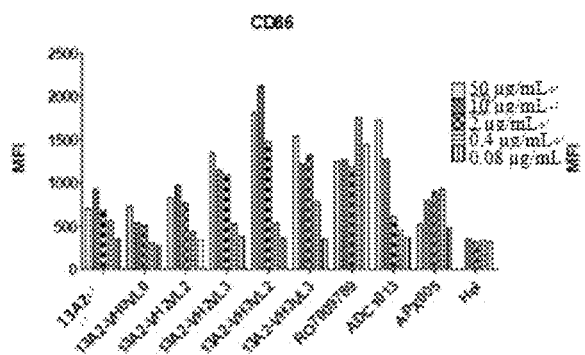
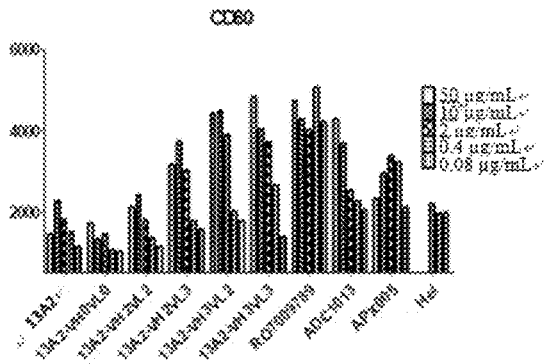
FIG. 10A　　　　　　　FIG. 10B
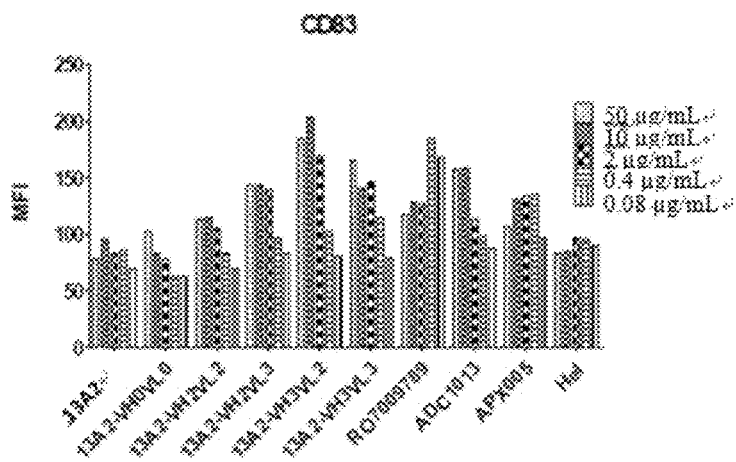
FIG. 10C

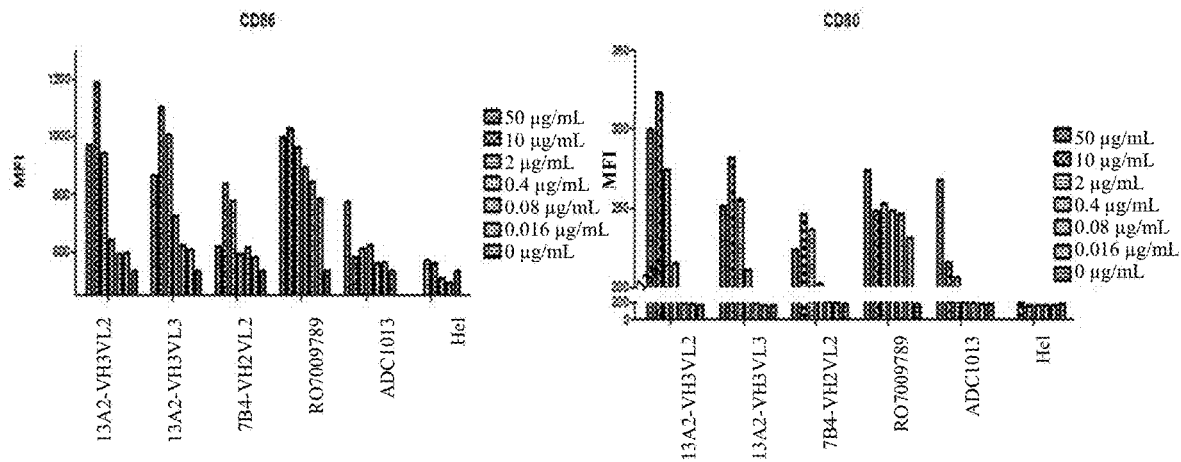
FIG. 11A  FIG. 11B
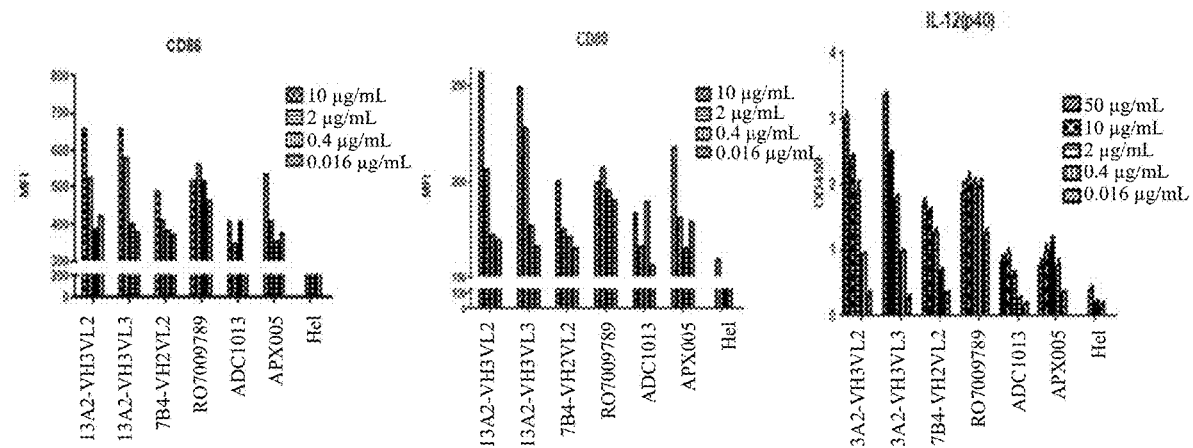
FIG. 12A  FIG. 12B  FIG. 12C

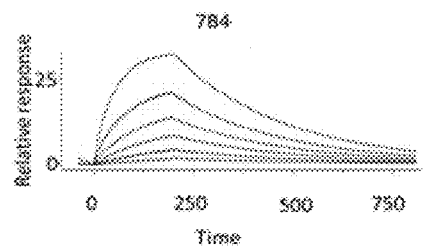
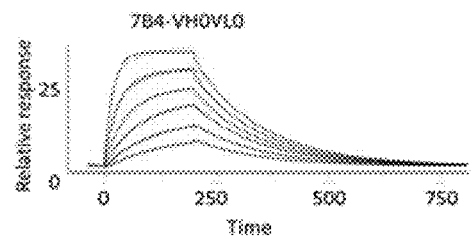
FIG. 13A  FIG. 13B
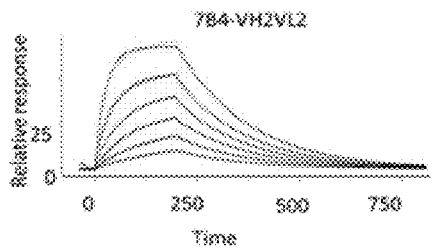
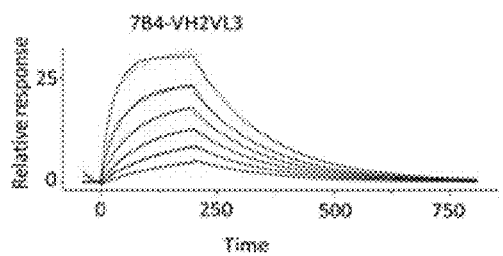
FIG. 13C  FIG. 13D
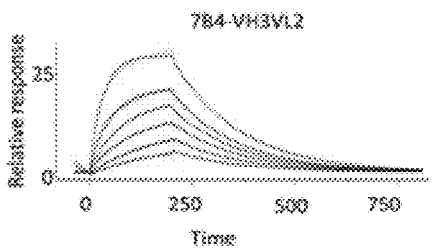
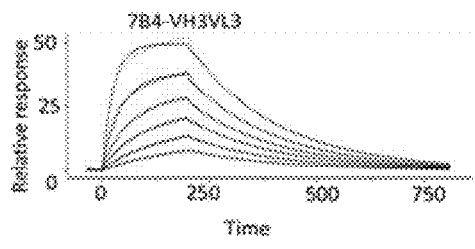
FIG. 13E  FIG. 13F
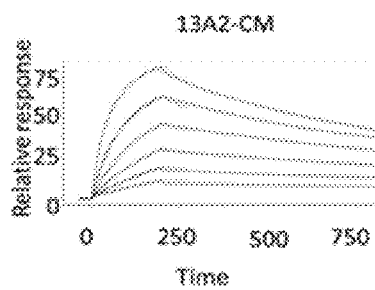
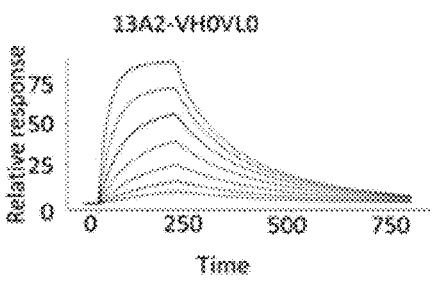
FIG. 13G  FIG. 13H

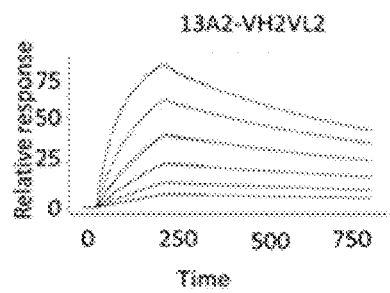 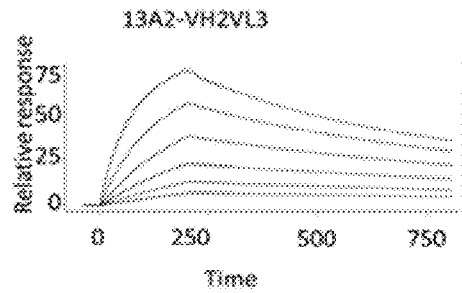
FIG. 13I          FIG. 13J
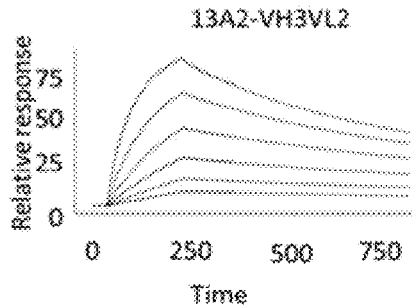 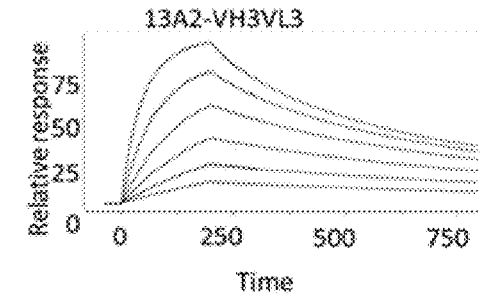
FIG. 13K          FIG. 13L
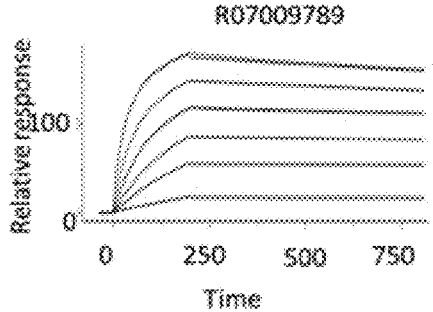 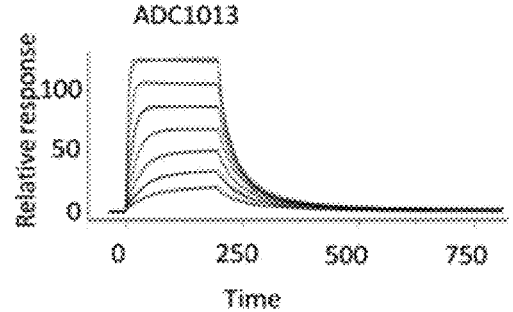
FIG. 13M          FIG. 13N

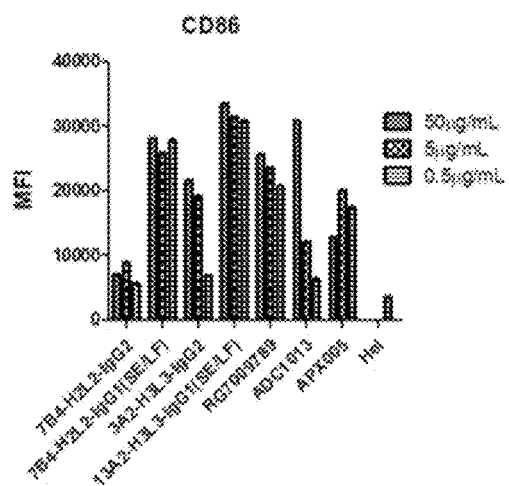 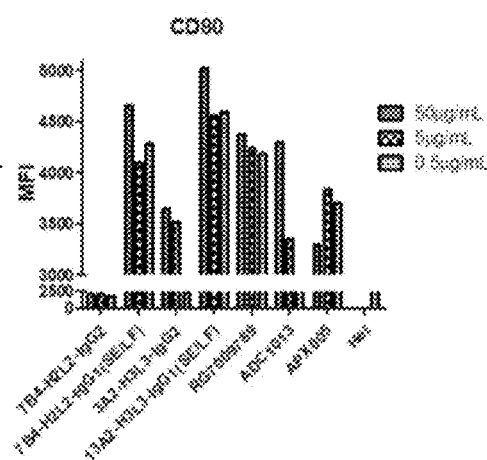
FIG. 16A  FIG. 16B
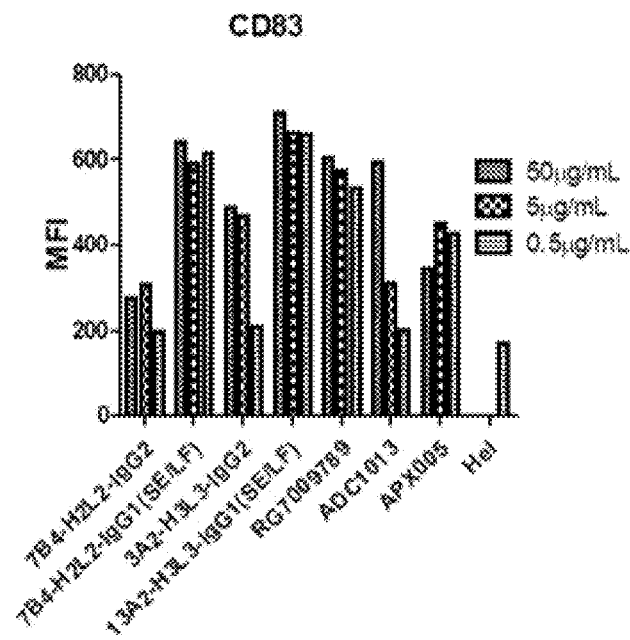
FIG. 16C

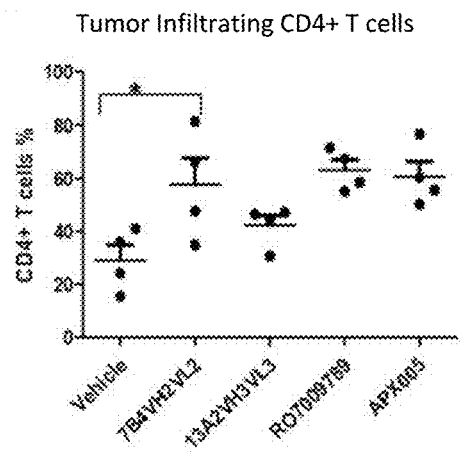 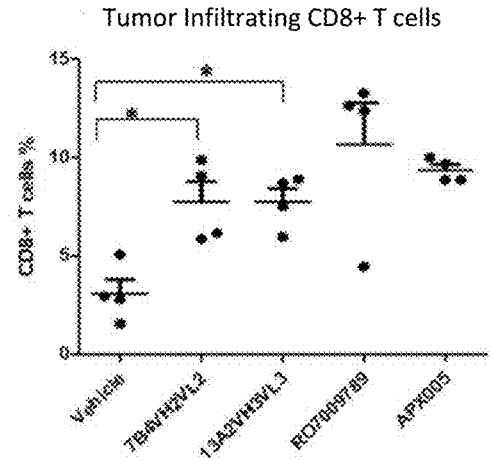
FIG. 19A  FIG. 19B
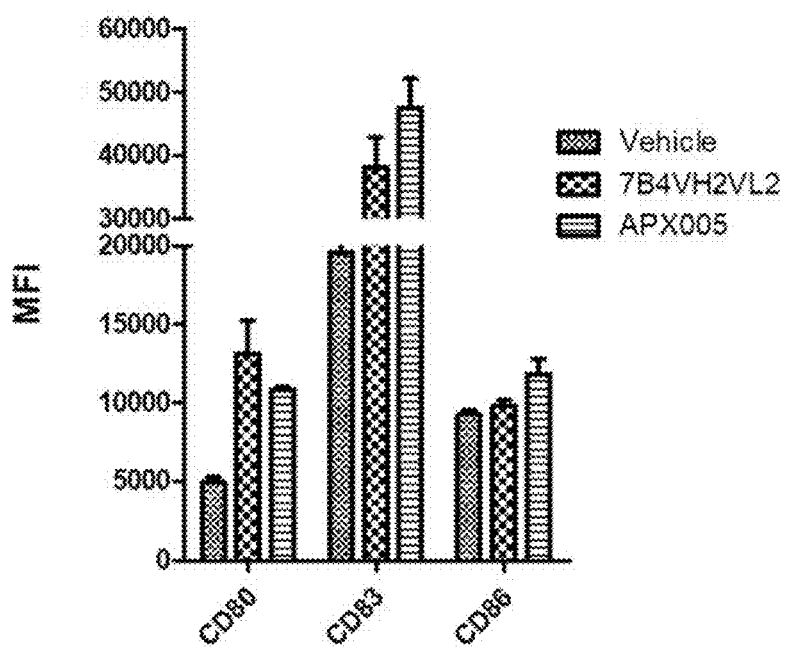
FIG. 20

SEQUENCE LISTING

```
<160> NUMBER OF SEQ ID NOS: 84

<210> SEQ ID NO 1
<211> LENGTH: 6
<212> TYPE: PRT
<213> ORGANISM: Artificial Sequence
<220> FEATURE:
<223> OTHER INFORMATION: 13A2/7B4-HV-CDR1

<400> SEQUENCE: 1

Thr Asn Tyr Tyr Trp Asn
1               5

<210> SEQ ID NO 2
<211> LENGTH: 6
<212> TYPE: PRT
<213> ORGANISM: Artificial Sequence
<220> FEATURE:
<223> OTHER INFORMATION: 16A6-HV-CDR1

<400> SEQUENCE: 2

Thr Asn Tyr His Trp Asn
1               5

<210> SEQ ID NO 3
<211> LENGTH: 6
<212> TYPE: PRT
<213> ORGANISM: Artificial Sequence
<220> FEATURE:
<223> OTHER INFORMATION: 29A10-HV-CDR1

<400> SEQUENCE: 3

Ser His Tyr Tyr Met Tyr
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: 92F6-HV-CDR1

<400> SEQUENCE: 4

Asp Thr Tyr Met His
1               5

<210> SEQ ID NO 5
<211> LENGTH: 5
<212> TYPE: PRT
<213> ORGANISM: Artificial Sequence
<220> FEATURE:
<223> OTHER INFORMATION: 77D9-HV-CDR1

<400> SEQUENCE: 5

Asn Tyr Ala Met Ser
1               5

<210> SEQ ID NO 6
<211> LENGTH: 5
<212> TYPE: PRT
<213> ORGANISM: Artificial Sequence
<220> FEATURE:
<223> OTHER INFORMATION: 50F6-HV-CDR1

<400> SEQUENCE: 6

Thr Tyr Trp Ile Asn
1               5

<210> SEQ ID NO 7
<211> LENGTH: 5
<212> TYPE: PRT
<213> ORGANISM: Artificial Sequence
<220> FEATURE:
<223> OTHER INFORMATION: 142F7-HV-CDR1

<400> SEQUENCE: 7

Asn Tyr Leu Ile Glu
1               5

<210> SEQ ID NO 8
<211> LENGTH: 16
<212> TYPE: PRT
<213> ORGANISM: Artificial Sequence
<220> FEATURE:
<223> OTHER INFORMATION: 13A2-HV-CDR2

<400> SEQUENCE: 8

Tyr Ile Asn Tyr Asp Gly Ser Asn Asn Tyr Asn Pro Ser Leu Lys Asn
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: 7B4/16A6-HV-CDR2

<400> SEQUENCE: 9

Tyr Ile Lys Tyr Asp Gly Ser Asn Asn Tyr Asn Pro Ser Leu Lys Asn
1               5                   10                  15
```

```
<210> SEQ ID NO 10
<211> LENGTH: 17
<212> TYPE: PRT
<213> ORGANISM: Artificial Sequence
<220> FEATURE:
<223> OTHER INFORMATION: 29A10-HV-CDR2

<400> SEQUENCE: 10

Thr Ile Ser Asp Ala Gly Ser Tyr Thr Tyr Tyr Ser Asp Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: 92F6-HV-CDR2

<400> SEQUENCE: 11

Arg Ile Asp Pro Ala Asn Gly Asn Thr Asn Tyr Asp Pro Lys Phe Gln
1               5                   10                  15

Gly

<210> SEQ ID NO 12
<211> LENGTH: 19
<212> TYPE: PRT
<213> ORGANISM: Artificial Sequence
<220> FEATURE:
<223> OTHER INFORMATION: 77D9-HV-CDR2

<400> SEQUENCE: 12

Glu Val Ser Gly Ser Gly Tyr Tyr Thr Tyr Tyr Pro Asp Thr Val Thr
1               5                   10                  15

Gly Arg Phe

<210> SEQ ID NO 13
<211> LENGTH: 17
<212> TYPE: PRT
<213> ORGANISM: Artificial Sequence
<220> FEATURE:
<223> OTHER INFORMATION: 50F6-HV-CDR2

<400> SEQUENCE: 13

Arg Ile Ser Pro Gly Ser Gly Ser Thr His Tyr Asn Glu Met Phe Lys
1               5                   10                  15

Gly

<210> SEQ ID NO 14
<211> LENGTH: 15
<212> TYPE: PRT
<213> ORGANISM: Artificial Sequence
<220> FEATURE:
<223> OTHER INFORMATION: 142F7-HV-CDR2

<400> SEQUENCE: 14

Asn Pro Gly Thr Gly Gly Thr Asn Tyr Asn Glu Lys Phe Lys Asp
1               5                   10                  15

<210> SEQ ID NO 15
<211> LENGTH: 3
<212> TYPE: PRT
<213> ORGANISM: Artificial Sequence
<220> FEATURE:
<223> OTHER INFORMATION: 13A2/7B4/16A6-HV-CDR3
```

<400> SEQUENCE: 15

Leu Asp Tyr
1

<210> SEQ ID NO 16
<211> LENGTH: 8
<212> TYPE: PRT
<213> ORGANISM: Artificial Sequence
<220> FEATURE:
<223> OTHER INFORMATION: 29A10-HV-CDR3

<400> SEQUENCE: 16

Gly Gly Tyr Trp Phe Phe Asp Val
1               5

<210> SEQ ID NO 17
<211> LENGTH: 9
<212> TYPE: PRT
<213> ORGANISM: Artificial Sequence
<220> FEATURE:
<223> OTHER INFORMATION: 92F6-HV-CDR3

<400> SEQUENCE: 17

Trp Gly Tyr Asp Trp Tyr Phe Asp Val
1               5

<210> SEQ ID NO 18
<211> LENGTH: 3
<212> TYPE: PRT
<213> ORGANISM: Artificial Sequence
<220> FEATURE:
<223> OTHER INFORMATION: 77D9-HV-CDR3

<400> SEQUENCE: 18

Arg Ala Tyr
1

<210> SEQ ID NO 19
<211> LENGTH: 3
<212> TYPE: PRT
<213> ORGANISM: Artificial Sequence
<220> FEATURE:
<223> OTHER INFORMATION: 50F6-HV-CDR3

<400> SEQUENCE: 19

Asn Asp Tyr
1

<210> SEQ ID NO 20
<211> LENGTH: 7
<212> TYPE: PRT
<213> ORGANISM: Artificial Sequence
<220> FEATURE:
<223> OTHER INFORMATION: 142F7-HV-CDR3

<400> SEQUENCE: 20

Gly Gly Ser Gly Phe Ala Tyr
1               5

<210> SEQ ID NO 21
<211> LENGTH: 16
<212> TYPE: PRT
<213> ORGANISM: Artificial Sequence
<220> FEATURE:
<223> OTHER INFORMATION: 13A2/7B4/16A6-LV-CDR1

```
<400> SEQUENCE: 21

Arg Ser Ser Gln Ser Leu Glu Asn Ser Asn Gly Asn Thr Phe Leu Asn
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: 29A10-LV-CDR1

<400> SEQUENCE: 22

Glu Ser Ser Gln Ser Leu Leu Tyr Ser Ser Asn Gln Lys Asn Tyr Leu
1               5                   10                  15

Ala

<210> SEQ ID NO 23
<211> LENGTH: 10
<212> TYPE: PRT
<213> ORGANISM: Artificial Sequence
<220> FEATURE:
<223> OTHER INFORMATION: 92F6-LV-CDR1

<400> SEQUENCE: 23

Ser Ala Ser Ser Ser Val Ser Tyr Ile His
1               5                   10

<210> SEQ ID NO 24
<211> LENGTH: 16
<212> TYPE: PRT
<213> ORGANISM: Artificial Sequence
<220> FEATURE:
<223> OTHER INFORMATION: 77D9-LV-CDR1

<400> SEQUENCE: 24

Arg Ser Ser Gln Ser Ile Val Leu Thr Asn Gly Asn Thr Tyr Leu Glu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: 50F6-LV-CDR1

<400> SEQUENCE: 25

Arg Ser Ser Gln Ser Ile Val Asn Ser Asn Gly Asn Thr Tyr Leu Glu
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: 142F7-LV-CDR1

<400> SEQUENCE: 26

Arg Ala Ser Gln Asp Ile Asn Asn Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: 13A2/7B4/16A6/77D9/50F6-LV-CDR2
```

```
<400> SEQUENCE: 27

Lys Val Ser Asn Arg Phe Ser
1               5

<210> SEQ ID NO 28
<211> LENGTH: 7
<212> TYPE: PRT
<213> ORGANISM: Artificial Sequence
<220> FEATURE:
<223> OTHER INFORMATION: 29A10-LV-CDR2

<400> SEQUENCE: 28

Trp Ala Ser Thr Arg Glu Ser
1               5

<210> SEQ ID NO 29
<211> LENGTH: 7
<212> TYPE: PRT
<213> ORGANISM: Artificial Sequence
<220> FEATURE:
<223> OTHER INFORMATION: 92F6-LV-CDR2

<400> SEQUENCE: 29

Thr Thr Ala Asn Leu Ala Ser
1               5

<210> SEQ ID NO 30
<211> LENGTH: 7
<212> TYPE: PRT
<213> ORGANISM: Artificial Sequence
<220> FEATURE:
<223> OTHER INFORMATION: 142F7-LV-CDR2

<400> SEQUENCE: 30

Tyr Thr Ser Arg Leu His Ser
1               5

<210> SEQ ID NO 31
<211> LENGTH: 9
<212> TYPE: PRT
<213> ORGANISM: Artificial Sequence
<220> FEATURE:
<223> OTHER INFORMATION: 13A2/7B4/16A6-LV-CDR3

<400> SEQUENCE: 31

Leu Gln Val Thr His Val Pro Phe Thr
1               5

<210> SEQ ID NO 32
<211> LENGTH: 9
<212> TYPE: PRT
<213> ORGANISM: Artificial Sequence
<220> FEATURE:
<223> OTHER INFORMATION: 29A10-LV-CDR3

<400> SEQUENCE: 32

Gln Gln Tyr Tyr Arg Ser Pro Leu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: 92F6-LV-CDR3
```

```
<400> SEQUENCE: 33

Gln Gln Arg Ser Asn Tyr Pro Phe Thr
1               5

<210> SEQ ID NO 34
<211> LENGTH: 9
<212> TYPE: PRT
<213> ORGANISM: Artificial Sequence
<220> FEATURE:
<223> OTHER INFORMATION: 77D9-LV-CDR3

<400> SEQUENCE: 34

Phe Gln Gly Ser His Val Pro Tyr Thr
1               5

<210> SEQ ID NO 35
<211> LENGTH: 9
<212> TYPE: PRT
<213> ORGANISM: Artificial Sequence
<220> FEATURE:
<223> OTHER INFORMATION: 50F6-LV-CDR3

<400> SEQUENCE: 35

Phe Gln Gly Ser His Val Pro Leu Thr
1               5

<210> SEQ ID NO 36
<211> LENGTH: 7
<212> TYPE: PRT
<213> ORGANISM: Artificial Sequence
<220> FEATURE:
<223> OTHER INFORMATION: 142F7-LV-CDR3

<400> SEQUENCE: 36

Gln Gln Gly Asn Thr Leu Pro
1               5

<210> SEQ ID NO 37
<211> LENGTH: 112
<212> TYPE: PRT
<213> ORGANISM: Artificial Sequence
<220> FEATURE:
<223> OTHER INFORMATION: 13A2-HV

<400> SEQUENCE: 37

Glu Val Lys Leu Glu Gln Ser Gly Pro Gly Leu Val Lys Pro Ser Gln
1               5                   10                  15

Ser Leu Ser Leu Thr Cys Ser Val Thr Gly Tyr Ser Ile Thr Thr Asn
            20                  25                  30

Tyr Tyr Trp Asn Trp Ile Arg Gln Phe Pro Gly Asn Lys Leu Glu Trp
        35                  40                  45

Met Gly Tyr Ile Asn Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Leu Asp Tyr Trp Gly Gln Gly Thr Ser Val Thr Val Ser Ser
            100                 105                 110

<210> SEQ ID NO 38
<211> LENGTH: 112
<212> TYPE: PRT
```

-continued

```
<213> ORGANISM: Artificial Sequence
<220> FEATURE:
<223> OTHER INFORMATION: 7B4-HV

<400> SEQUENCE: 38

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Thr Asn
            20                  25                  30

Tyr Tyr Trp Asn Trp Ile Arg Gln Phe Pro Gly Asn Lys Leu Glu Trp
        35                  40                  45

Met Gly Tyr Ile Lys Tyr Asp Gly Ser Asn Asn Tyr Asn Pro Ser Leu
50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Leu Asp Tyr Trp Gly Gln Gly Thr Ser Val Thr Val Ser Ser
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: 16A6-HV

<400> SEQUENCE: 39

Glu Val Gln Leu Glu Gln Ser Gly Pro Gly Leu Val Lys Pro Ser Gln
1               5                   10                  15

Ser Leu Ser Leu Thr Cys Ser Val Thr Gly Tyr Ser Ile Thr Thr Asn
            20                  25                  30

Tyr His Trp Asn Trp Ile Arg Gln Phe Pro Gly Asn Lys Leu Glu Trp
        35                  40                  45

Met Gly Tyr Ile Lys Tyr Asp Gly Ser Asn Asn Tyr Asn Pro Ser Leu
50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Leu Asp Tyr Trp Gly Gln Gly Thr Ser Val Thr Val Ser Ser
            100                 105                 110

<210> SEQ ID NO 40
<211> LENGTH: 123
<212> TYPE: PRT
<213> ORGANISM: Artificial Sequence
<220> FEATURE:
<223> OTHER INFORMATION: 29A10-HV

<400> SEQUENCE: 40

Gln Val Lys Leu Glu Gln Ser Gly Gly Gly Leu Val Lys Pro Gly Gly
1               5                   10                  15

Ser Leu Lys Leu Ser Cys Ala Ala Ser Gly Phe Thr Phe Ser His Tyr
            20                  25                  30

Tyr Met Tyr Trp Val Arg Gln Thr Pro Glu Lys Arg Leu Glu Trp Val
        35                  40                  45

Ala Thr Ile Ser Asp Ala Gly Ser Tyr Thr Tyr Tyr Ser Asp Ser Val
50                  55                  60
```

Lys Gly Arg Phe Thr Ile Ser Arg Asp Asn Ala Lys Asn Leu Tyr
65                  70                  75                  80

Leu Gln Met Ser Ser Leu Lys Ser Asp Asp Thr Ala Met Tyr Phe Cys
                85                  90                  95

Ala Arg Thr Tyr Tyr Arg Gly Asp Gly Gly Tyr Trp Phe Phe Asp Val
            100                 105                 110

Trp Gly Ala Gly Thr Ala Val Thr Val Ser Ser
        115                 120

<210> SEQ ID NO 41
<211> LENGTH: 118
<212> TYPE: PRT
<213> ORGANISM: Artificial Sequence
<220> FEATURE:
<223> OTHER INFORMATION: 92F6-HV

<400> SEQUENCE: 41

Gln Val Gln Leu Glu Gln Ser Gly Ala Glu Val Val Lys Pro Gly Ala
1               5                   10                  15

Ser Val Lys Val Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Asn Tyr Asp Pro Lys Phe
    50                  55                  60

Gln Gly Lys Ala Thr Ile Thr Ala Asp Thr Ser Ser Asn Thr Gly Tyr
65                  70                  75                  80

Leu Gln Leu Ser Ser Leu Thr Ser Glu Asp Thr Ala Val Tyr Tyr Cys
                85                  90                  95

Ser Arg Trp Gly Tyr Asp Trp Tyr Phe Asp Val Trp Gly Ala Gly Thr
            100                 105                 110

Ser Val Thr Val Ser Ser
        115

<210> SEQ ID NO 42
<211> LENGTH: 112
<212> TYPE: PRT
<213> ORGANISM: Artificial Sequence
<220> FEATURE:
<223> OTHER INFORMATION: 77D9-HV

<400> SEQUENCE: 42

Gln Val Lys Leu Glu Glu Ser Gly Gly Gly Leu Val Lys Pro Gly Gly
1               5                   10                  15

Ser Leu Lys Leu Ser Cys Ala Ala Ser Gly Phe Thr Phe Arg Asn Tyr
            20                  25                  30

Ala Met Ser Trp Val Arg Gln Ser Pro Gly Glu Arg Leu Glu Trp Val
        35                  40                  45

Ala Glu Val Ser Gly Ser Gly Tyr Tyr Thr Tyr Tyr Pro Asp Thr Val
    50                  55                  60

Thr Gly Arg Phe Thr Ile Ser Arg Asp Asn Ala Asn Asn Thr Leu Tyr
65                  70                  75                  80

Leu Glu Val Ser Ser Leu Arg Ser Glu Asp Thr Ala Met Tyr Tyr Cys
                85                  90                  95

Thr Ser Arg Ala Tyr Trp Gly Gln Gly Thr Leu Val Thr Val Ser Ala
            100                 105                 110

```
<210> SEQ ID NO 43
<211> LENGTH: 112
<212> TYPE: PRT
<213> ORGANISM: Artificial Sequence
<220> FEATURE:
<223> OTHER INFORMATION: 50F6-HV

<400> SEQUENCE: 43
```

Gln Val Gln Leu Glu Gln Ser Gly Asp Asp Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Ile Asn Trp Ile Lys Gln Arg Pro Gly Gln Gly Leu Glu Trp Ile
        35                  40                  45

Gly Arg Ile Ser Pro Gly Ser Gly Ser Thr His Tyr Asn Glu Met Phe
    50                  55                  60

Lys Gly Lys Ala Thr Leu Thr Val Asp Thr Ser Ser Ser Thr Ala Tyr
65                  70                  75                  80

Ile Gln Leu Ser Ser Leu Ser Ser Glu Asp Ser Ala Val Tyr Phe Cys
                85                  90                  95

Thr Arg Asn Asp Tyr Trp Gly Gln Gly Thr Thr Leu Thr Val Ser Ser
            100                 105                 110

```
<210> SEQ ID NO 44
<211> LENGTH: 116
<212> TYPE: PRT
<213> ORGANISM: Artificial Sequence
<220> FEATURE:
<223> OTHER INFORMATION: 142F7-HV

<400> SEQUENCE: 44
```

Glu Val Gln Leu Glu Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Gly Ile Gln Arg Pro Gly Gln Gly Leu Glu Trp Ile
        35                  40                  45

Gly Val Ile Asn Pro Gly Thr Gly Gly Thr Asn Tyr Asn Glu Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Gly Gly Ser Gly Phe Ala Tyr Trp Gly Gln Gly Thr Leu Val
            100                 105                 110

Thr Val Ser Ala
        115

```
<210> SEQ ID NO 45
<211> LENGTH: 112
<212> TYPE: PRT
<213> ORGANISM: Artificial Sequence
<220> FEATURE:
<223> OTHER INFORMATION: 13A2-VH0VL0-HV

<400> SEQUENCE: 45
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Thr Asn
            20                  25                  30

Tyr Tyr Trp Asn Trp Ile Arg Gln Pro Pro Gly Lys Gly Leu Glu Trp
                35                  40                  45

Ile Gly Tyr Ile Asn Tyr Asp Gly Ser Asn Asn Tyr Asn Pro Ser Leu
 50                  55                  60

Lys Asn Arg Val Thr Met Ser Val Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Leu Asp Tyr Trp Gly Gln Gly Thr Leu Val Thr Val Ser Ser
                100                 105                 110

<210> SEQ ID NO 46
<211> LENGTH: 112
<212> TYPE: PRT
<213> ORGANISM: Artificial Sequence
<220> FEATURE:
<223> OTHER INFORMATION: 13A2-VH2VL2/VH2VL3-HV

<400> SEQUENCE: 46

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Thr Thr Asn
                20                  25                  30

Tyr Tyr Trp Asn Trp Ile Arg Gln Pro Pro Gly Lys Gly Leu Glu Trp
                35                  40                  45

Met Gly Tyr Ile Asn Tyr Asp Gly Ser Asn Asn Tyr Asn Pro Ser Leu
 50                  55                  60

Lys Asn Arg Ile Thr Ile Ser Val Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Leu Asp Tyr Trp Gly Gln Gly Thr Leu Val Thr Val Ser Ser
                100                 105                 110

<210> SEQ ID NO 47
<211> LENGTH: 112
<212> TYPE: PRT
<213> ORGANISM: Artificial Sequence
<220> FEATURE:
<223> OTHER INFORMATION: 13A2-VH3VL2/VH3VL3-HV

<400> SEQUENCE: 47

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Thr Thr Asn
                20                  25                  30

Tyr Tyr Trp Asn Trp Ile Arg Gln Pro Pro Gly Asn Lys Leu Glu Trp
                35                  40                  45

Met Gly Tyr Ile Asn Tyr Asp Gly Ser Asn Asn Tyr Asn Pro Ser Leu
 50                  55                  60

Lys Asn Arg Ile Thr Ile Ser Val Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Leu Asp Tyr Trp Gly Gln Gly Thr Leu Val Thr Val Ser Ser
                100                 105                 110

```
<210> SEQ ID NO 48
<211> LENGTH: 112
<212> TYPE: PRT
<213> ORGANISM: Artificial Sequence
<220> FEATURE:
<223> OTHER INFORMATION: 7B4-VH0VL0-HV

<400> SEQUENCE: 48
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Thr Asn
            20                  25                  30

Tyr Tyr Trp Asn Trp Ile Arg Gln Pro Pro Gly Lys Gly Leu Glu Trp
        35                  40                  45

Ile Gly Tyr Ile Lys Tyr Asp Gly Ser Asn Asn Tyr Asn Pro Ser Leu
    50                  55                  60

Lys Asn Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Leu Asp Tyr Trp Gly Gln Gly Thr Leu Val Thr Val Ser Ser
            100                 105                 110

```
<210> SEQ ID NO 49
<211> LENGTH: 112
<212> TYPE: PRT
<213> ORGANISM: Artificial Sequence
<220> FEATURE:
<223> OTHER INFORMATION: 7B4-VH2VL2/VH2VL3-HV

<400> SEQUENCE: 49
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Thr Asn
            20                  25                  30

Tyr Tyr Trp Asn Trp Ile Arg Gln Pro Pro Gly Lys Gly Leu Glu Trp
        35                  40                  45

Met Gly Tyr Ile Lys Tyr Asp Gly Ser Asn Asn Tyr Asn Pro Ser Leu
    50                  55                  60

Lys Asn Arg Ile Thr Ile Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Leu Asp Tyr Trp Gly Gln Gly Thr Leu Val Thr Val Ser Ser
            100                 105                 110

```
<210> SEQ ID NO 50
<211> LENGTH: 112
<212> TYPE: PRT
<213> ORGANISM: Artificial Sequence
<220> FEATURE:
<223> OTHER INFORMATION: 7B4-VH3VL2/7B4-VH3VL3-HV

<400> SEQUENCE: 50
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Thr Asn
            20                  25                  30

Tyr Tyr Trp Asn Trp Ile Arg Gln Pro Pro Gly Asn Lys Leu Glu Trp
        35                  40                  45

```
Met Gly Tyr Ile Lys Tyr Asp Gly Ser Asn Asn Tyr Asn Pro Ser Leu
        50                  55                  60

Lys Asn Arg Ile Thr Ile Ser Val Asp Thr Ser Lys Asn Gln Phe Ser
 65                  70                  75                  80

Leu Lys Leu Ser Ser Val Thr Ala Val Asp Thr Ala Val Tyr Tyr Cys
                85                  90                  95

Ala Arg Leu Asp Tyr Trp Gly Gln Gly Thr Leu Val Thr Val Ser Ser
            100                 105                 110

<210> SEQ ID NO 51
<211> LENGTH: 112
<212> TYPE: PRT
<213> ORGANISM: Artificial Sequence
<220> FEATURE:
<223> OTHER INFORMATION: 13A2-LV

<400> SEQUENCE: 51

Asp Ile Val Met Thr Gln Ser Pro Leu Ser Leu Pro Val Ser Leu Gly
 1                   5                  10                  15

Asp Gln Ala Ser Ile Ser Cys Arg Ser Ser Gln Ser Leu Glu Asn Ser
                20                  25                  30

Asn Gly Asn Thr Phe Leu Asn Trp Phe Leu Gln Lys Pro Gly Gln Ser
            35                  40                  45

Pro Gln Leu Leu Ile Tyr Lys Val Ser Asn Arg Phe Ser Gly Val Leu
        50                  55                  60

Asp Arg Phe Ser Gly Thr Gly Ser Gly Thr Asp Phe Thr Leu Thr Ile
 65                  70                  75                  80

Ser Arg Val Glu Ala Glu Asp Leu Gly Val Tyr Phe Cys Leu Gln Val
                85                  90                  95

Thr His Val Pro Phe Thr Phe Gly Ser Gly Thr Lys Leu Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: 7B4-LV

<400> SEQUENCE: 52

Asp Ile Val Leu Thr Gln Ser Pro Leu Ser Leu Pro Val Ser Leu Gly
 1                   5                  10                  15

Asp Gln Ala Ser Ile Ser Cys Arg Ser Ser Gln Ser Leu Glu Asn Ser
                20                  25                  30

Asn Gly Asn Thr Phe Leu Asn Trp Phe Leu Gln Lys Pro Gly Gln Ser
            35                  40                  45

Pro Gln Leu Leu Ile Tyr Lys Val Ser Asn Arg Phe Ser Gly Val Leu
        50                  55                  60

Asp Arg Phe Ser Gly Thr Gly Ser Gly Thr Asp Phe Thr Leu Thr Ile
 65                  70                  75                  80

Ser Arg Val Glu Ala Glu Asp Leu Gly Val Tyr Phe Cys Leu Gln Val
                85                  90                  95

Thr His Val Pro Phe Thr Phe Gly Ser Gly Thr Lys Leu Glu Ile Lys
            100                 105                 110

<210> SEQ ID NO 53
<211> LENGTH: 112
<212> TYPE: PRT
```

<213> ORGANISM: Artificial Sequence
<220> FEATURE:
<223> OTHER INFORMATION: 16A6-LV

<400> SEQUENCE: 53

```
Asp Ile Val Leu Thr Gln Ser Thr Leu Ser Leu Ser Val Ser Leu Gly
1               5                   10                  15
Asp Gln Ala Ser Ile Ser Cys Arg Ser Gln Ser Leu Glu Asn Ser
            20                  25                  30
Asn Gly Asn Thr Phe Leu Asn Trp Phe Leu Gln Lys Pro Gly Gln Ser
        35                  40                  45
Pro Gln Leu Leu Ile Tyr Lys Val Ser Asn Arg Phe Ser Gly Val Leu
    50                  55                  60
Asp Arg Phe Ser Gly Thr Gly Ser Gly Thr Asp Leu Thr Leu Thr Ile
65                  70                  75                  80
Ser Arg Val Glu Ala Glu Asp Leu Gly Val Tyr Phe Cys Leu Gln Val
                85                  90                  95
Thr His Val Pro Phe Thr Phe Gly Ser Gly Thr Lys Leu Glu Ile Lys
            100                 105                 110
```

<210> SEQ ID NO 54
<211> LENGTH: 113
<212> TYPE: PRT
<213> ORGANISM: Artificial Sequence
<220> FEATURE:
<223> OTHER INFORMATION: 29A10-LV

<400> SEQUENCE: 54

```
Asp Ile Val Ile Thr Gln Ser Thr Ser Ser Leu Ala Val Ser Val Gly
1               5                   10                  15
Glu Lys Val Thr Met Ser Cys Glu Ser Ser Gln Ser Leu Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Tyr Trp Ala Ser Thr Arg Glu Ser Gly Val
    50                  55                  60
Pro Asp Arg Phe Thr Ala Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
Tyr Tyr Arg Ser Pro Leu Thr Phe Gly Ala Gly Thr Lys Leu Glu Leu
            100                 105                 110
Lys
```

<210> SEQ ID NO 55
<211> LENGTH: 106
<212> TYPE: PRT
<213> ORGANISM: Artificial Sequence
<220> FEATURE:
<223> OTHER INFORMATION: 92F6-LV

<400> SEQUENCE: 55

```
Asp Ile Val Ile Thr Gln Ser Thr Ala Ile Met Ser Ala Ser Pro Gly
1               5                   10                  15
Glu Lys Val Thr Ile Thr Cys Ser Ala Ser Ser Val Ser Tyr Ile
            20                  25                  30
His Trp Phe Gln Gln Lys Pro Gly Thr Ser Pro Lys Leu Trp Ile Tyr
        35                  40                  45
```

```
Thr Thr Ala Asn Leu Ala Ser Gly Val Pro Ala Arg Phe Ser Gly Ser
     50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Asn Tyr Pro Phe Thr
                 85                  90                  95

Phe Gly Ser Gly Thr Lys Leu Glu Ile Lys
                100                 105
```

<210> SEQ ID NO 56
<211> LENGTH: 113
<212> TYPE: PRT
<213> ORGANISM: Artificial Sequence
<220> FEATURE:
<223> OTHER INFORMATION: 77D9-LV

<400> SEQUENCE: 56

```
Asp Ile Val Met Thr Gln Ser Pro Thr Leu Ser Leu Pro Val Ser Leu
 1               5                  10                  15

Gly Asp Gln Ala Ser Ile Ser Cys Arg Ser Ser Gln Ser Ile Val Leu
                 20                  25                  30

Thr Asn Gly Asn Thr Tyr Leu Glu Trp Tyr Leu Gln Arg Pro Gly Gln
             35                  40                  45

Ser Pro Lys Leu Leu Ile Tyr Lys Val Ser Asn Arg Phe Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Leu Gly Val Tyr Tyr Cys Phe Gln
                 85                  90                  95

Gly Ser His Val Pro Tyr Thr Phe Gly Gly Gly Thr Lys Leu Glu Ile
                100                 105                 110

Lys
```

<210> SEQ ID NO 57
<211> LENGTH: 112
<212> TYPE: PRT
<213> ORGANISM: Artificial Sequence
<220> FEATURE:
<223> OTHER INFORMATION: 50F6-LV

<400> SEQUENCE: 57

```
Asp Ile Val Leu Thr Gln Ser Pro Leu Ser Leu Pro Val Ser Leu Gly
 1               5                  10                  15

Asp Gln Ala Ser Ile Ser Cys Arg Ser Ser Gln Ser Ile Val Asn Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Leu Thr Phe Gly Ala Gly Thr Lys Leu Glu Leu Lys
                100                 105                 110
```

<210> SEQ ID NO 58
<211> LENGTH: 107

```
<212> TYPE: PRT
<213> ORGANISM: Artificial Sequence
<220> FEATURE:
<223> OTHER INFORMATION: 142F7-LV

<400> SEQUENCE: 58

Asp Ile Val Leu Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 59
<211> LENGTH: 112
<212> TYPE: PRT
<213> ORGANISM: Artificial Sequence
<220> FEATURE:
<223> OTHER INFORMATION: 13A2-VH0VL0/7B4-VH0VL0-LV

<400> SEQUENCE: 59

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Gly Asn Thr Phe Leu Asn Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Phe Thr Phe Gly Gln Gly Thr Lys Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: 13A2-VH2VL2/VH3VL2/7B4-VH2VL2/VH3VL2-LV

<400> SEQUENCE: 60

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Gly Asn Thr Phe Leu Asn Trp Phe Gln Gln Arg Pro Gly Gln Ser
        35                  40                  45

Pro Arg Leu Leu Ile Tyr Lys Val Ser Asn Arg Phe Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                     85                  90                  95

Thr His Val Pro Phe Thr Phe Gly Gln Gly Thr Lys Leu Glu Ile Lys
                 100                 105                 110

<210> SEQ ID NO 61
<211> LENGTH: 112
<212> TYPE: PRT
<213> ORGANISM: Artificial Sequence
<220> FEATURE:
<223> OTHER INFORMATION: 13A2-VH2VL3/VH3VL3/7B4-VH2VL3/VH3VL3-LV

<400> SEQUENCE: 61

Asp Val Val Leu Thr Gln Ser Pro Leu Ser Leu Pro Val Thr Leu Gly
  1               5                  10                  15

Gln Pro Ala Ser Ile Ser Cys Arg Ser Ser Gln Ser Leu Glu Asn Ser
                 20                  25                  30

Asn Gly Asn Thr Phe Leu Asn Trp Phe Gln Gln Arg Pro Gly Gln Ser
                 35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Leu Gln Val
                     85                  90                  95

Thr His Val Pro Phe Thr Phe Gly Ser Gly Thr Lys Leu Glu Ile Lys
                 100                 105                 110

<210> SEQ ID NO 62
<211> LENGTH: 324
<212> TYPE: PRT
<213> ORGANISM: Artificial Sequence
<220> FEATURE:
<223> OTHER INFORMATION: Mouse IgG1 heavy chain constant region

<400> SEQUENCE: 62

Ala Lys Thr Thr Pro Pro Ser Val Tyr Pro Leu Ala Pro Gly Ser Ala
  1               5                  10                  15

Ala Gln Thr Asn Ser Met Val Thr Leu Gly Cys Leu Val Lys Gly Tyr
                 20                  25                  30

Phe Pro Glu Pro Val Thr Val Thr Trp Asn Ser Gly Ser Leu Ser Ser
                 35                  40                  45

Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                     85                  90                  95

Ile Val Pro Arg Asp Cys Gly Cys Lys Pro Cys Ile Cys Thr Val Pro
                 100                 105                 110

Glu Val Ser Ser Val Phe Ile Phe Pro Pro Lys Pro Lys Asp Val Leu
                 115                 120                 125

Thr Ile Thr Leu Thr Pro Lys Val Thr Cys Val Val Val Asp Ile Ser
                 130                 135                 140
```

-continued

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Thr Lys Gly Arg Pro Lys Ala Pro Gln
210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
        290                 295                 300

Leu His Glu Gly Leu His Asn His Thr Glu Lys Ser Leu Ser His
305                 310                 315                 320

Ser Pro Gly Lys

<210> SEQ ID NO 63
<211> LENGTH: 326
<212> TYPE: PRT
<213> ORGANISM: Artificial Sequence
<220> FEATURE:
<223> OTHER INFORMATION: Human IgG2 heavy chain constant region

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp

```
                180              185              190
Leu Asn Gly Lys Glu Tyr Lys Cys Lys Val Ser Asn Lys Gly Leu Pro
            195              200              205

Ala Pro Ile Glu Lys Thr Ile Ser Lys Thr Lys Gly Gln Pro Arg Glu
        210              215              220

Pro Gln Val Tyr Thr Leu Pro Pro Ser Arg Glu Met Thr Lys Asn
225              230              235              240

Gln Val Ser Leu Thr Cys Leu Val Lys Gly Phe Tyr Pro Ser Asp Ile
            245              250              255

Ala Val Glu Trp Glu Ser Asn Gly Gln Pro Glu Asn Asn Tyr Lys Thr
        260              265              270

Thr Pro Pro Met Leu Asp Ser Asp Gly Ser Phe Phe Leu Tyr Ser Lys
        275              280              285

Leu Thr Val Asp Lys Ser Arg Trp Gln Gln Gly Asn Val Phe Ser Cys
        290              295              300

Ser Val Met His Glu Ala Leu His Asn His Tyr Thr Gln Lys Ser Leu
305              310              315              320

Ser Leu Ser Pro Gly Lys
            325

<210> SEQ ID NO 64
<211> LENGTH: 330
<212> TYPE: PRT
<213> ORGANISM: Artificial Sequence
<220> FEATURE:
<223> OTHER INFORMATION: Human IgG1 heavy chain constant region with
      S267E and L328F mutations

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Phe Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 107
<212> TYPE: PRT
<213> ORGANISM: Artificial Sequence
<220> FEATURE:
<223> OTHER INFORMATION: Human kappa light chain constant region

<400> SEQUENCE: 65

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 66
<211> LENGTH: 107
<212> TYPE: PRT
<213> ORGANISM: Artificial Sequence
<220> FEATURE:
<223> OTHER INFORMATION: mouse kappa light chain constant region

<400> SEQUENCE: 66

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
                20                  25                  30

Tyr Pro Lys Asp Ile Asn Val Lys Trp Lys Ile Asp Gly Ser Glu Arg
                35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80
```

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 67
<211> LENGTH: 834
<212> TYPE: DNA
<213> ORGANISM: Homo sapiens

<400> SEQUENCE: 67

| | | | | | | |
|---|---|---|---|---|---|---|
| atggttcgtc | tgcctctgca | gtgcgtcctc | tggggctgct | tgctgaccgc | tgtccatcca |  60 |
| gaaccaccca | ctgcatgcag | agaaaaacag | tacctaataa | acagtcagtg | ctgttctttg | 120 |
| tgccagccag | gacagaaact | ggtgagtgac | tgcacagagt | tcactgaaac | ggaatgcctt | 180 |
| ccttgcggtg | aaagcgaatt | cctagacacc | tggaacagag | agacacactg | ccaccagcac | 240 |
| aaatactgcg | accccaacct | agggcttcgg | gtccagcaga | agggcacctc | agaaacagac | 300 |
| accatctgca | cctgtgaaga | aggctggcac | tgtacgagtg | aggcctgtga | gagctgtgtc | 360 |
| ctgcaccgct | catgctcgcc | cggctttggg | gtcaagcaga | ttgctacagg | ggtttctgat | 420 |
| accatctgcg | agccctgccc | agtcggcttc | ttctccaatg | tgtcatctgc | tttcgaaaaa | 480 |
| tgtcaccctt | ggacaagctg | tgagaccaaa | gacctggttg | tgcaacaggc | aggcacaaac | 540 |
| aagactgatg | ttgtctgtgg | tccccaggat | cggctgagag | ccctggtggt | gatccccatc | 600 |
| atcttcggga | tcctgtttgc | catcctcttg | gtgctggtct | ttatcaaaaa | ggtggccaag | 660 |
| aagccaacca | ataaggcccc | ccacccccaag | caggaacccc | aggagatcaa | ttttcccgac | 720 |
| gatcttcctg | ctccaacac | tgctgctcca | gtgcaggaga | ctttacatgg | atgccaaccg | 780 |
| gtcacccagg | aggatggcaa | agagagtcgc | atctcagtgc | aggagagaca | gtga | 834 |

<210> SEQ ID NO 68
<211> LENGTH: 277
<212> TYPE: PRT
<213> ORGANISM: Homo sapiens

<400> SEQUENCE: 68

Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
                20                  25                  30

Ile Asn Ser Gln Cys Cys Ser Leu Cys Gln Pro Gly Gln Lys Leu Val
                35                  40                  45

Ser Asp Cys Thr Glu Phe Thr Glu Thr Glu Cys Leu Pro Cys Gly Glu
            50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
                115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys

```
            145                 150                 155                 160
Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
                195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275

<210> SEQ ID NO 69
<211> LENGTH: 837
<212> TYPE: PRT
<213> ORGANISM: Macaca mulatta

<400> SEQUENCE: 69

Ala Thr Gly Gly Thr Thr Cys Gly Thr Cys Thr Gly Cys Cys Thr Cys
1               5                   10                  15

Thr Gly Cys Ala Gly Thr Gly Cys Gly Thr Cys Cys Thr Cys Thr Gly
            20                  25                  30

Gly Gly Gly Cys Thr Gly Cys Thr Thr Gly Cys Thr Gly Ala Cys Cys
        35                  40                  45

Gly Cys Thr Gly Thr Cys Thr Ala Thr Cys Ala Gly Ala Ala Cys Cys
    50                  55                  60

Cys Ala Cys Cys Cys Ala Cys Thr Gly Cys Ala Thr Gly Cys Ala Gly
65                  70                  75                  80

Ala Gly Ala Ala Ala Ala Cys Ala Gly Thr Ala Cys Cys Thr Ala Ala
                85                  90                  95

Ala Thr Ala Ala Ala Cys Ala Gly Thr Cys Ala Gly Thr Gly Cys Thr
                100                 105                 110

Gly Thr Thr Cys Thr Thr Thr Gly Thr Gly Cys Cys Ala Gly Cys Cys
        115                 120                 125

Ala Gly Gly Ala Cys Ala Gly Ala Ala Cys Thr Gly Gly Thr Gly Gly
    130                 135                 140

Ala Gly Thr Gly Ala Cys Thr Gly Cys Ala Gly Ala Gly Thr
145                 150                 155                 160

Thr Cys Ala Cys Cys Gly Ala Ala Cys Ala Gly Ala Ala Thr Gly
        165                 170                 175

Cys Cys Thr Thr Cys Cys Thr Gly Cys Ala Gly Thr Gly Ala Ala
            180                 185                 190

Ala Gly Cys Gly Ala Ala Thr Thr Cys Cys Thr Ala Gly Ala Cys Ala
        195                 200                 205

Cys Cys Thr Gly Gly Ala Ala Thr Ala Gly Ala Gly Ala Gly Ala Cys
    210                 215                 220

Ala Cys Gly Cys Thr Gly Cys Ala Cys Ala Gly Cys Ala Cys
225                 230                 235                 240
```

-continued

```
Ala Ala Ala Thr Ala Cys Thr Gly Cys Gly Ala Cys Cys Cys Cys Ala
                245                 250                 255

Ala Cys Cys Thr Ala Gly Gly Gly Cys Thr Thr Cys Gly Gly Gly Thr
            260                 265                 270

Cys Cys Ala Gly Cys Ala Gly Ala Ala Gly Gly Gly Cys Ala Cys Cys
        275                 280                 285

Thr Cys Ala Gly Ala Ala Ala Cys Ala Gly Ala Cys Ala Cys Cys Ala
    290                 295                 300

Thr Cys Thr Gly Cys Ala Cys Cys Thr Gly Thr Gly Ala Ala Gly Ala
305                 310                 315                 320

Ala Gly Gly Cys Cys Thr Gly Cys Ala Cys Thr Gly Thr Ala Thr Gly
                325                 330                 335

Ala Gly Thr Gly Ala Gly Thr Cys Cys Thr Gly Thr Gly Ala Gly Ala
            340                 345                 350

Gly Cys Thr Gly Thr Gly Thr Cys Cys Cys Gly Cys Ala Cys Cys Gly
        355                 360                 365

Cys Thr Cys Ala Thr Gly Cys Thr Thr Gly Cys Cys Thr Gly Gly Cys
    370                 375                 380

Thr Thr Thr Gly Gly Gly Gly Thr Cys Ala Ala Gly Cys Ala Gly Ala
385                 390                 395                 400

Thr Thr Gly Cys Thr Ala Cys Ala Gly Gly Gly Gly Thr Thr Thr Cys
                405                 410                 415

Thr Gly Ala Thr Ala Cys Cys Ala Thr Cys Thr Gly Thr Gly Ala Gly
            420                 425                 430

Cys Cys Cys Thr Gly Cys Cys Cys Gly Gly Thr Cys Gly Gly Cys Thr
        435                 440                 445

Thr Cys Thr Thr Cys Thr Cys Cys Ala Ala Thr Gly Thr Gly Thr Cys
    450                 455                 460

Ala Thr Cys Thr Gly Cys Thr Thr Thr Thr Gly Ala Ala Ala Ala Gly
465                 470                 475                 480

Thr Gly Thr Cys Gly Cys Cys Cys Thr Thr Gly Gly Ala Cys Ala Ala
                485                 490                 495

Gly Cys Thr Gly Thr Gly Ala Gly Ala Cys Cys Ala Ala Ala Gly Ala
            500                 505                 510

Cys Cys Thr Gly Gly Thr Thr Gly Thr Gly Cys Ala Ala Cys Ala Gly
        515                 520                 525

Gly Cys Ala Gly Gly Cys Ala Cys Ala Ala Ala Cys Ala Ala Gly Ala
    530                 535                 540

Cys Thr Gly Ala Thr Gly Thr Thr Gly Thr Cys Thr Gly Thr Gly Gly
545                 550                 555                 560

Thr Cys Cys Cys Cys Ala Gly Gly Ala Thr Cys Gly Gly Cys Ala Gly
                565                 570                 575

Ala Gly Ala Gly Cys Cys Cys Thr Gly Gly Thr Gly Gly Thr Gly Ala
            580                 585                 590

Thr Cys Cys Cys Cys Ala Thr Cys Thr Gly Cys Thr Thr Gly Gly Gly
        595                 600                 605

Gly Ala Thr Cys Cys Thr Gly Thr Thr Thr Gly Thr Cys Ala Thr Cys
    610                 615                 620

Cys Thr Cys Cys Thr Cys Thr Thr Gly Gly Thr Gly Cys Thr Gly Gly
625                 630                 635                 640

Thr Cys Thr Thr Thr Ala Thr Cys Ala Ala Ala Ala Ala Gly Gly Thr
                645                 650                 655

Gly Gly Cys Cys Ala Ala Gly Ala Ala Gly Cys Cys Ala Ala Ala Cys
```

```
                    660             665             670
Gly Ala Thr Ala Ala Gly Gly Cys Cys Cys Cys Cys Ala Cys Cys
            675             680             685

Cys Cys Ala Ala Gly Cys Ala Gly Gly Ala Ala Cys Cys Cys Ala
        690             695             700

Gly Gly Ala Gly Ala Thr Cys Ala Ala Thr Thr Thr Cys Thr Gly
705             710             715             720

Gly Ala Cys Gly Ala Thr Cys Thr Thr Cys Thr Gly Gly Cys Thr
                725             730             735

Cys Cys Ala Ala Cys Cys Cys Thr Gly Cys Cys Gly Cys Thr Cys Cys
            740             745             750

Ala Gly Thr Gly Cys Ala Gly Gly Ala Gly Ala Cys Thr Thr Thr Ala
            755             760             765

Cys Ala Thr Gly Gly Ala Thr Gly Cys Cys Ala Ala Cys Cys Ala Gly
        770             775             780

Thr Cys Ala Cys Cys Ala Gly Gly Ala Gly Gly Ala Thr Gly Gly
785             790             795             800

Cys Ala Ala Gly Ala Gly Ala Gly Thr Cys Gly Cys Ala Thr Cys
            805             810             815

Thr Cys Ala Gly Thr Gly Cys Ala Gly Gly Ala Gly Ala Gly Ala Cys
            820             825             830

Ala Gly Thr Gly Ala
        835

<210> SEQ ID NO 70
<211> LENGTH: 278
<212> TYPE: PRT
<213> ORGANISM: Macaca mulatta

<400> SEQUENCE: 70

Met Val Arg Leu Pro Leu Gln Cys Val Leu Trp Gly Cys Leu Leu Thr
1               5                   10                  15

Ala Val Tyr Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Ser Glu
    50                  55                  60

Ser Glu Phe Leu Asp Thr Trp Asn Arg Glu Thr Arg Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Leu His Cys Met
            100                 105                 110

Ser Glu Ser Cys Glu Ser Cys Val Pro His Arg Ser Cys Leu Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys Arg Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Gln
            180                 185                 190
```

Arg Ala Leu Val Val Ile Pro Ile Cys Leu Gly Ile Leu Phe Val Ile
            195                 200                 205

Leu Leu Leu Val Leu Val Phe Ile Lys Lys Val Ala Lys Lys Pro Asn
    210                 215                 220

Asp Lys Ala Pro His Pro Lys Gln Glu Pro Gln Glu Ile Asn Phe Leu
225                 230                 235                 240

Asp Asp Leu Pro Gly Ser Asn Pro Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln
        275

<210> SEQ ID NO 71
<211> LENGTH: 869
<212> TYPE: DNA
<213> ORGANISM: Mus musculus

<400> SEQUENCE: 71
atggtgtctt tgcctcggct gtgcgcgcta tggggctgct tgttgacagc ggtccatcta     60
gggcagtgtg ttacgtgcag tgacaaacag tacctccacg atggccagtg ctgtgatttg    120
tgccagccag aagccgact gacaagccac tgcacagctc ttgagaagac ccaatgccac    180
ccatgtgact caggcgaatt ctcagccag tggaacaggg agattcgctg tcaccagcac    240
agacactgtg aacccaatca agggcttcgg gttaagaagg agggcaccgc agaatcagac    300
actgtctgta cctgtaagga aggacaacac tgcaccagca aggattggag gcatgtgctc    360
agcacacgcc ctgtatccct ggctttggag ttatggagat ggccactgag accactgata    420
ccgtctgtca tccctgccca gtcggcttct tctccaatca gtcatcactt ttcgaaaagt    480
gttatccctg acaagctgt gaggataaga acttggaggt cctacagaaa ggaacgagtc    540
agactaatgt catctgtggt ttaaagtccc ggatgcgagc cctgctggtc attcctgtcg    600
tgatgggcat cctcatcacc attttcgggg tgtttctcta tatcaaaaag gtggtcaaga    660
aaccaaagga taatgagatc ttaccccctg cggctcgacg gcaagatccc caggagatgg    720
aagattatcc cggtcataac accgctgctc cagtgcagga gacgctgcac gggtgtcagc    780
ctgtcacaca ggaggatggt aaagagagtc gcatctcagt gcaggagcgg caggtgacag    840
acagcatagc cttgaggccc ctggtctga                                        869

<210> SEQ ID NO 72
<211> LENGTH: 289
<212> TYPE: PRT
<213> ORGANISM: Mus musculus

<400> SEQUENCE: 72

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

```
Arg His Cys Glu Pro Asn Gln Gly Leu Arg Val Lys Lys Glu Gly Thr
                85                  90                  95
Ala Glu Ser Asp Thr Val Cys Thr Cys Lys Glu Gly Gln His Cys Thr
            100                 105                 110
Ser Lys Asp Cys Glu Ala Cys Ala Gln His Thr Pro Cys Ile Pro Gly
        115                 120                 125
Phe Gly Val Met Glu Met Ala Thr Glu Thr Asp Thr Val Cys His
130                 135                 140
Pro Cys Pro Val Gly Phe Phe Ser Asn Gln Ser Ser Leu Phe Glu Lys
145                 150                 155                 160
Cys Tyr Pro Trp Thr Ser Cys Glu Asp Lys Asn Leu Glu Val Leu Gln
                165                 170                 175
Lys Gly Thr Ser Gln Thr Asn Val Ile Cys Gly Leu Lys Ser Arg Met
            180                 185                 190
Arg Ala Leu Leu Val Ile Pro Val Val Met Gly Ile Leu Ile Thr Ile
        195                 200                 205
Phe Gly Val Phe Leu Tyr Ile Lys Lys Val Val Lys Lys Pro Lys Asp
210                 215                 220
Asn Glu Ile Leu Pro Pro Ala Ala Arg Arg Gln Asp Pro Gln Glu Met
225                 230                 235                 240
Glu Asp Tyr Pro Gly His Asn Thr Ala Ala Pro Val Gln Glu Thr Leu
                245                 250                 255
His Gly Cys Gln Pro Val Thr Gln Glu Asp Gly Lys Glu Ser Arg Ile
            260                 265                 270
Ser Val Gln Glu Arg Gln Val Thr Asp Ser Ile Ala Leu Arg Pro Leu
        275                 280                 285
Val

<210> SEQ ID NO 73
<211> LENGTH: 173
<212> TYPE: PRT
<213> ORGANISM: Artificial Sequence
<220> FEATURE:
<223> OTHER INFORMATION: Full-length OD40 ECD

<400> SEQUENCE: 73

Glu Pro Pro Thr Ala Cys Arg Glu Lys Gln Tyr Leu Ile Asn Ser Gln
1               5                   10                  15
Cys Cys Ser Leu Cys Gln Pro Gly Gln Lys Leu Val Ser Asp Cys Thr
            20                  25                  30
Glu Phe Thr Glu Thr Glu Cys Leu Pro Cys Gly Glu Ser Glu Phe Leu
        35                  40                  45
Asp Thr Trp Asn Arg Glu Thr His Cys His Gln His Lys Tyr Cys Asp
50                  55                  60
Pro Asn Leu Gly Leu Arg Val Gln Gln Lys Gly Thr Ser Glu Thr Asp
65                  70                  75                  80
Thr Ile Cys Thr Cys Glu Glu Gly Trp His Cys Thr Ser Glu Ala Cys
                85                  90                  95
Glu Ser Cys Val Leu His Arg Ser Cys Ser Pro Gly Phe Gly Val Lys
            100                 105                 110
Gln Ile Ala Thr Gly Val Ser Asp Thr Ile Cys Glu Pro Cys Pro Val
        115                 120                 125
Gly Phe Phe Ser Asn Val Ser Ser Ala Phe Glu Lys Cys His Pro Trp
130                 135                 140
Thr Ser Cys Glu Thr Lys Asp Leu Val Val Gln Gln Ala Gly Thr Asn
```

```
145                 150                 155                 160

Lys Thr Asp Val Val Cys Gly Pro Gln Asp Arg Leu Arg
                165                 170

<210> SEQ ID NO 74
<211> LENGTH: 133
<212> TYPE: PRT
<213> ORGANISM: Artificial Sequence
<220> FEATURE:
<223> OTHER INFORMATION: Truncant 1

<400> SEQUENCE: 74

Pro Cys Gly Glu Ser Glu Phe Leu Asp Thr Trp Asn Arg Glu Thr His
1               5                   10                  15

Cys His Gln His Lys Tyr Cys Asp Pro Asn Leu Gly Leu Arg Val Gln
            20                  25                  30

Gln Lys Gly Thr Ser Glu Thr Asp Thr Ile Cys Thr Cys Glu Glu Gly
        35                  40                  45

Trp His Cys Thr Ser Glu Ala Cys Glu Ser Cys Val Leu His Arg Ser
    50                  55                  60

Cys Ser Pro Gly Phe Gly Val Lys Gln Ile Ala Thr Gly Val Ser Asp
65                  70                  75                  80

Thr Ile Cys Glu Pro Cys Pro Val Gly Phe Phe Ser Asn Val Ser Ser
                85                  90                  95

Ala Phe Glu Lys Cys His Pro Trp Thr Ser Cys Glu Thr Lys Asp Leu
            100                 105                 110

Val Val Gln Gln Ala Gly Thr Asn Lys Thr Asp Val Val Cys Gly Pro
        115                 120                 125

Gln Asp Arg Leu Arg
    130

<210> SEQ ID NO 75
<211> LENGTH: 90
<212> TYPE: PRT
<213> ORGANISM: Artificial Sequence
<220> FEATURE:
<223> OTHER INFORMATION: Truncant 2

<400> SEQUENCE: 75

Thr Cys Glu Glu Gly Trp His Cys Thr Ser Glu Ala Cys Glu Ser Cys
1               5                   10                  15

Val Leu His Arg Ser Cys Ser Pro Gly Phe Gly Val Lys Gln Ile Ala
            20                  25                  30

Thr Gly Val Ser Asp Thr Ile Cys Glu Pro Cys Pro Val Gly Phe Phe
        35                  40                  45

Ser Asn Val Ser Ser Ala Phe Glu Lys Cys His Pro Trp Thr Ser Cys
    50                  55                  60

Glu Thr Lys Asp Leu Val Val Gln Gln Ala Gly Thr Asn Lys Thr Asp
65                  70                  75                  80

Val Val Cys Gly Pro Gln Asp Arg Leu Arg
                85                  90

<210> SEQ ID NO 76
<211> LENGTH: 50
<212> TYPE: PRT
<213> ORGANISM: Artificial Sequence
<220> FEATURE:
<223> OTHER INFORMATION: Truncant 3

<400> SEQUENCE: 76
```

Glu Pro Cys Pro Val Gly Phe Phe Ser Asn Val Ser Ala Phe Glu
1               5                   10                  15

Lys Cys His Pro Trp Thr Ser Cys Glu Thr Lys Asp Leu Val Val Gln
            20                  25                  30

Gln Ala Gly Thr Asn Lys Thr Asp Val Val Cys Gly Pro Gln Asp Arg
        35                  40                  45

Leu Arg
    50

<210> SEQ ID NO 77
<211> LENGTH: 156
<212> TYPE: PRT
<213> ORGANISM: Artificial Sequence
<220> FEATURE:
<223> OTHER INFORMATION: Truncant 4

<400> SEQUENCE: 77

Cys Ser Leu Cys Gln Pro Gly Gln Lys Leu Val Ser Asp Cys Thr Glu
1               5                   10                  15

Phe Thr Glu Thr Glu Cys Leu Pro Cys Gly Glu Ser Glu Phe Leu Asp
            20                  25                  30

Thr Trp Asn Arg Glu Thr His Cys His Gln His Lys Tyr Cys Asp Pro
        35                  40                  45

Asn Leu Gly Leu Arg Val Gln Gln Lys Gly Thr Ser Glu Thr Asp Thr
    50                  55                  60

Ile Cys Thr Cys Glu Glu Gly Trp His Cys Thr Ser Glu Ala Cys Glu
65                  70                  75                  80

Ser Cys Val Leu His Arg Ser Cys Ser Pro Gly Phe Gly Val Lys Gln
                85                  90                  95

Ile Ala Thr Gly Val Ser Asp Thr Ile Cys Glu Pro Cys Pro Val Gly
            100                 105                 110

Phe Phe Ser Asn Val Ser Ser Ala Phe Glu Lys Cys His Pro Trp Thr
        115                 120                 125

Ser Cys Glu Thr Lys Asp Leu Val Val Gln Gln Ala Gly Thr Asn Lys
    130                 135                 140

Thr Asp Val Val Cys Gly Pro Gln Asp Arg Leu Arg
145                 150                 155

<210> SEQ ID NO 78
<211> LENGTH: 150
<212> TYPE: PRT
<213> ORGANISM: Artificial Sequence
<220> FEATURE:
<223> OTHER INFORMATION: Truncant 5

<400> SEQUENCE: 78

Glu Pro Pro Thr Ala Cys Arg Glu Lys Gln Tyr Leu Ile Asn Ser Gln
1               5                   10                  15

Cys Pro Cys Gly Glu Ser Glu Phe Leu Asp Thr Trp Asn Arg Glu Thr
            20                  25                  30

His Cys His Gln His Lys Tyr Cys Asp Pro Asn Leu Gly Leu Arg Val
        35                  40                  45

Gln Gln Lys Gly Thr Ser Glu Thr Asp Thr Ile Cys Thr Cys Glu Glu
    50                  55                  60

Gly Trp His Cys Thr Ser Glu Ala Cys Glu Ser Cys Val Leu His Arg
65                  70                  75                  80

Ser Cys Ser Pro Gly Phe Gly Val Lys Gln Ile Ala Thr Gly Val Ser

```
                      85                  90                  95
Asp Thr Ile Cys Glu Pro Cys Pro Val Gly Phe Phe Ser Asn Val Ser
                100                 105                 110

Ser Ala Phe Glu Lys Cys His Pro Trp Thr Ser Cys Glu Thr Lys Asp
            115                 120                 125

Leu Val Val Gln Gln Ala Gly Thr Asn Lys Thr Asp Val Val Cys Gly
        130                 135                 140

Pro Gln Asp Arg Leu Arg
145                 150

<210> SEQ ID NO 79
<211> LENGTH: 173
<212> TYPE: PRT
<213> ORGANISM: Artificial Sequence
<220> FEATURE:
<223> OTHER INFORMATION: Mutant 1

<400> SEQUENCE: 79

Glu Pro Pro Thr Ala Cys Ala Ala Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170

<210> SEQ ID NO 80
<211> LENGTH: 173
<212> TYPE: PRT
<213> ORGANISM: Artificial Sequence
<220> FEATURE:
<223> OTHER INFORMATION: Mutant 2

<400> SEQUENCE: 80

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Ala
            20                  25                  30

Ala Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60
```

```
Pro Asn Leu Gly Leu Arg Val Gln Gln Lys Gly Thr Ser Glu Thr Asp
 65                  70                  75                  80

Thr Ile Cys Thr Cys Glu Glu Gly Trp His Cys Thr Ser Glu Ala Cys
                 85                  90                  95

Glu Ser Cys Val Leu His Arg Ser Cys Ser Pro Gly Phe Gly Val Lys
                100                 105                 110

Gln Ile Ala Thr Gly Val Ser Asp Thr Ile Cys Glu Pro Cys Pro Val
            115                 120                 125

Gly Phe Phe Ser Asn Val Ser Ser Ala Phe Glu Lys Cys His Pro Trp
        130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170
```

<210> SEQ ID NO 81
<211> LENGTH: 173
<212> TYPE: PRT
<213> ORGANISM: Artificial Sequence
<220> FEATURE:
<223> OTHER INFORMATION: Mutant 3

<400> SEQUENCE: 81

```
Glu Pro Pro Thr Ala Cys Arg Glu Lys Gln Tyr Leu Ile Asn Ser Gln
 1               5                  10                  15

Cys Cys Ser Leu Cys Gln Pro Gly Gln Lys Leu Val Ser Asp Cys Thr
                20                  25                  30

Glu Ala Ala Glu Thr Glu Cys Leu Pro Cys Gly Glu Ser Glu Phe Leu
            35                  40                  45

Asp Thr Trp Asn Arg Glu Thr His Cys His Gln His Lys Tyr Cys Asp
        50                  55                  60

Pro Asn Leu Gly Leu Arg Val Gln Gln Lys Gly Thr Ser Glu Thr Asp
 65                  70                  75                  80

Thr Ile Cys Thr Cys Glu Glu Gly Trp His Cys Thr Ser Glu Ala Cys
                 85                  90                  95

Glu Ser Cys Val Leu His Arg Ser Cys Ser Pro Gly Phe Gly Val Lys
                100                 105                 110

Gln Ile Ala Thr Gly Val Ser Asp Thr Ile Cys Glu Pro Cys Pro Val
            115                 120                 125

Gly Phe Phe Ser Asn Val Ser Ser Ala Phe Glu Lys Cys His Pro Trp
        130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170
```

<210> SEQ ID NO 82
<211> LENGTH: 173
<212> TYPE: PRT
<213> ORGANISM: Artificial Sequence
<220> FEATURE:
<223> OTHER INFORMATION: Mutant 4

<400> SEQUENCE: 82

```
Glu Pro Pro Thr Ala Cys Arg Glu Lys Gln Tyr Leu Ile Asn Ser Gln
 1               5                  10                  15

Cys Cys Ser Leu Cys Gln Pro Gly Gln Lys Leu Val Ser Asp Cys Thr
                20                  25                  30
```

```
Glu Phe Thr Ala Ala Glu Cys Leu Pro Cys Gly Ser Glu Phe Leu
            35                  40                  45

Asp Thr Trp Asn Arg Glu Thr His Cys His Gln His Lys Tyr Cys Asp
 50                  55                  60

Pro Asn Leu Gly Leu Arg Val Gln Gln Lys Gly Thr Ser Glu Thr Asp
 65                  70                  75                  80

Thr Ile Cys Thr Cys Glu Glu Gly Trp His Cys Thr Ser Glu Ala Cys
                 85                  90                  95

Glu Ser Cys Val Leu His Arg Ser Cys Ser Pro Gly Phe Gly Val Lys
                100                 105                 110

Gln Ile Ala Thr Gly Val Ser Asp Thr Ile Cys Glu Pro Cys Pro Val
                115                 120                 125

Gly Phe Phe Ser Asn Val Ser Ser Ala Phe Glu Lys Cys His Pro Trp
        130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170

<210> SEQ ID NO 83
<211> LENGTH: 19
<212> TYPE: PRT
<213> ORGANISM: Artificial Sequence
<220> FEATURE:
<223> OTHER INFORMATION: Signal peptide

<400> SEQUENCE: 83

Met Gly Trp Ser Cys Ile Ile Leu Phe Leu Val Ala Thr Ala Thr Gly
  1               5                  10                  15

Val His Ser

<210> SEQ ID NO 84
<211> LENGTH: 324
<212> TYPE: PRT
<213> ORGANISM: Artificial Sequence
<220> FEATURE:
<223> OTHER INFORMATION: mFc-tag

<400> SEQUENCE: 84

Ala Lys Thr Thr Pro Pro Ser Val Tyr Pro Leu Ala Pro Gly Ser Ala
  1               5                  10                  15

Ala Gln Thr Asn Ser Met Val Thr Leu Gly Cys Leu Val Lys Gly Tyr
                 20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140
```

```
Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys
```

ANTIBODIES TARGETING CD40 AND USES THEREOF

FIELD OF THE INVENTION

The invention relates to an antibody specifically binding to human CD40, preparation and use thereof, especially its use in treatment of human diseases associated with CD40, such as cancers, inflammatory diseases, infectious diseases, atherothrombosis, and respiratory diseases.

BACKGROUND OF THE INVENTION

CD40, also referred to as tumor necrosis factor receptor superfamily member 5 or TNFR5, is a transmembrane costimulatory protein expressed on antigen presenting cells such as B cells, macrophages, and dendritic cells. Binding of this protein with CD40L (CD154), the major ligand expressed primarily by activated T lymphocytes and platelets, activates antigen presenting cells and triggers a variety of downstream signalings, including immune cell activation and proliferation, and production of cytokines and chemokines, enhancing cellular and immune functions (Ara A et al., (2018) *Immunotargets Ther* 7: 55-61).

On the other hand, CD40 is also found on non-immune cells and tumors (Costello et al., (1999) *Immunol Today* 20(11): 488-493; Tong et al., (2003) *Cancer Gene Ther* 10(1): 1-13; Lee et al., (2014) *Curr Cancer Drug Targets* 14(7): 610-620; Ara A et al., (2018) supra), and was reported to be involved in pathologies of several inflammatory diseases, including autoimmune diseases, atherothrombosis, cancers, and respiratory diseases. For example, CD40/CD40L expression was up-regulated in atheroma-associated cells. CD40 was found in neally all B-cell malignancies and up to 70% of solid tumors, and CD40 engagement in certain B-cell malignancies caused increased expression of many factors that protect the cell from apoptosis induced by apoptotic agents (Lee et al., (1999) *Proc Natl Acad Sci USA* 96:9136-9141).

Despite of CD40's complicated effects on tumor development, several anti-CD40 antibodies have been developed for potential tumor treatment. CP-870,893, a fully human IgG2 CD40 agonistic antibody developed by Pfizer, can activate dendritic cells and has shown clinical efficacy in a number of settings of patients with advanced cancers (Vonderheide et al., (2007) *J Clin Oncol* 25(7): 876-883; Gladue et al., (2011) *Cancer Immunol Immunother* 60(7): 1009-1017; Beatty et al., (2013) *Expert Rev Anticancer Ther* 17(2): 175-186; Vonderheide et al., (2013) *Oncoimmunology* 2(1): e23033; Nowak et al., *Ann Oncol* 26(12): 2483-2490; 2015 U.S. Pat. No. 7,338,660). Dacetuzumab, also known as SGN-40, a humanized IgG1 agonistic anti-CD40 antibody developed by Seattle Genetics, has also shown anti-tumor activity when given intravenously every week, especially in patients with diffuse large B-cell lymphoma. Preclinical data also showed synergic effect of Dacetuzumab with other agents such as the anti-CD20 mAb rituximab (Lapalombella et al., (2009) *Br J Haematol* 144(6): 848-855; Hussein et al., (2010) *Haematologica* 95(5): 845-848; de Vos et al., (2014) *J Hematol Oncol* 7: 44). Chi Lob 7/4, another chimeric anti-human IgG1 agonistic anti-CD40 antibody developed by Cancer Research UK, is undergoing initial clinical testing. Eleven of the 21 patients showed stable disease with no complete or partial responses (Chowdhury et al., (2014) *Cancer Immunol Res* 2(3): 229-240). Further, antagonistic anti-CD40 antibodies have been studied for their anti-tumor activity on human multiple myeloma and chronic lymphocytic leukemia (Bensinger W et al., (2012) *Br J Haematol.* 159(1): 58-66; Mohammad Luqman et al., (2008) *Blood* 112: 711-720).

There remains a need for more CD40 antibodies with improved pharmaceutical characteristics.

SUMMARY OF THE INVENTION

The present invention provides an isolated monoclonal antibody, for example, a mouse, human, chimeric or humanized monoclonal antibody, that binds to CD40 (e.g., the human CD40, and monkey CD40). It may be an agonistic CD40 antibody that activates CD40 signaling.

The antibody of the invention can be used for a variety of applications, including detection of the CD40 protein, and treatment and prevention of CD40 associated diseases, such as cancers, inflammatory diseases, infectious diseases, atherothrombosis, and respiratory diseases.

Accordingly, in one aspect, the invention pertains to an isolated monoclonal antibody (e.g., a humanized antibody), or an antigen-binding portion thereof, that binds CD40, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, or 99% identity to, or set forth in (1) SEQ ID NOs: 1, 8 and 15, respectively; (2) SEQ ID NOs: 1, 9 and 15, respectively; (3) SEQ ID NOs: 2, 9 and 15, respectively; (4) SEQ ID NOs: 3, 10 and 16, respectively; (5) SEQ ID NOs: 4, 11 and 17, respectively; (6) SEQ ID NOs: 5, 12 and 18, respectively; (7) SEQ ID NOs: 6, 13 and 19, respectively; or (8) SEQ ID NOs: 7, 14 and 20, respectively; wherein, the antibody, or antigen-binding fragment thereof, binds to CD40.

In one aspect, an isolated monoclonal antibody, or an antigen-binding portion thereof, of the present invention comprises a heavy chain variable region comprising an amino acid sequence having at least 80%, 85%, 90%, 95%, 98% or 99% identity to, or set forth in SEQ ID NOs: 37, 38, 39, 40, 41, 42, 43, 44, 45, 46, 47, 48, 49 or 50, wherein the antibody or antigen-binding fragment thereof binds to CD40.

In one aspect, an isolated monoclonal antibody, or an antigen-binding portion thereof, of the present invention comprises a light chain variable region that comprises a CDR1 region, a CDR2 region and a CDR3 region, wherein the CDR1 region, the CDR2 region, and the CDR3 region comprise amino acid sequences having at least 80%, 85%, 90%, 95%, 98% or 99% identity to, or set forth in (1) SEQ ID NOs: 21, 27 and 31, respectively; (2) SEQ ID NOs: 22, 28 and 32, respectively; (3) SEQ ID NOs: 23, 29 and 33, respectively; (4) SEQ ID NOs: 24, 27 and 34, respectively; (5) SEQ ID NOs: 25, 27 and 35, respectively; or (6) SEQ ID NOs: 26, 30 and 36, respectively; wherein the antibody or antigen-binding fragment thereof binds to CD40.

In one aspect, an isolated monoclonal antibody, or an antigen-binding portion thereof, of the present invention comprises a light chain variable region comprising an amino acid sequence having at least 80%, 85%, 90%, 95%, 98% or 99% identity to, or set forth in SEQ ID NOs: 51, 52, 53, 54, 55, 56, 57, 58, 59, 60, or 61, wherein the antibody or antigen-binding fragment thereof binds to CD40.

In one aspect, an isolated monoclonal antibody, or an antigen-binding portion thereof, of the present invention comprises a heavy chain variable region and a light chain variable region each comprises a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98% or 99% identity to, or set forth in (1) SEQ ID NOs: 1, 8, 15, 21, 27 and 31, respectively; (2) SEQ ID NOs: 1, 9, 15, 21, 27 and 31, respectively; (3) 2, 9, 15, 21, 27 and 31, respectively; (4) SEQ ID NOs: 3, 10, 16, 22, 28 and 32, respectively; (5) SEQ ID NOs: 4, 11, 17, 23, 29 and 33, respectively; (6) SEQ ID NOs: 5, 12, 18, 24, 27 and 34, respectively; (7) SEQ ID NOs: 6, 13, 19, 25, 27 and 35, respectively; or (8) SEQ ID NOs: 7, 14, 20 26, 30 and 36, respectively, wherein the antibody or antigen-binding fragment thereof binds to CD40.

In one embodiment, an isolated monoclonal antibody, or the antigen-binding portion thereof, of the present invention comprises a heavy chain variable region and a light chain variable region, the heavy chain variable region and the light chain variable region comprising amino acid sequences having at least 80%, 85%, 90%, 95%, 98% or 99% identity to, or set forth in (1) SEQ ID NOs: 37 and 51, respectively; (2) SEQ ID NOs: 38 and 52, respectively; (3) SEQ ID NOs: 39 and 53, respectively; (4) SEQ ID NOs: 40 and 54, respectively; (5) SEQ ID NOs: 41 and 55, respectively; (6) SEQ ID NOs: 44 and 58, respectively; (7) SEQ ID NOs: 45 and 59, respectively; (8) SEQ ID NOs: 46 and 60, respectively; (9) SEQ ID NOs: 46 and 61, respectively; (10) SEQ ID NOs: 47 and 60, respectively; (11) SEQ ID NOs: 47 and 61, respectively; (12) SEQ ID NOs: 48 and 59, respectively; (13) SEQ ID NOs: 49 and 60, respectively; (14) SEQ ID NOs: 49 and 61, respectively; (15) SEQ ID NOs: 50 and 60, respectively; (16) SEQ ID NOs: 50 and 61, respectively; (17) SEQ ID NOs: 42 and 56, respectively; or (18) SEQ ID NOs: 43 and 57, respectively, wherein the antibody or antigen-binding fragment thereof binds to CD40.

In one embodiment, an isolated monoclonal antibody, or the antigen-binding portion thereof, of the present invention comprises a heavy chain and a light chain, the heavy chain comprising a heavy chain variable region and a heavy chain constant region, the light chain comprising a light chain variable region and a light chain constant region, wherein, the heavy chain constant region comprises amino acid sequences having at least 80%, 85%, 90%, 95%, 98% or 99% identity to, or set forth in SEQ ID Nos: 62, 63 or 64, and the light chain constant region comprises amino acid sequences having at least 80%, 85%, 90%, 95%, 98% or 99% identity to, or set forth in SEQ ID Nos: 65 or 66, and the heavy chain variable region and the light chain variable region comprise amino acid sequences described above, wherein the antibody or antigen-binding fragment thereof binds to CD40.

The antibody of the present invention in some embodiments comprises or consists of two heavy chains and two light chains, wherein each heavy chain comprises the heavy chain constant region, heavy chain variable region or CDR sequences mentioned above, and each light chain comprises the light chain constant region, light chain variable region or CDR sequences mentioned above, wherein the antibody binds to CD40. The antibody of the invention can be a full-length antibody, for example, of an IgG1, IgG2 or IgG4 isotype. The antibody of the present invention in other embodiments may be a single chain antibody, or consists of antibody fragments, such as Fab or Fab'2 fragments.

The antibody, or antigen-binding fragment, of the present invention binds specifically to human and monkey CD40, and blocks or promotes CD40-CD40L interaction. Agonistic CD40 antibodies of the present invention, able to activate CD40 signaling and drive maturation of immune cells such as dendritic cells, have in vivo anti-tumor effect comparable to or better than prior art anti-CD40 agnostic antibodies, with equal or less toxicity. Tumors would not grow, or even totally vanish, even after antibody administration has stopped.

The invention also provides an immunoconjugate comprising an antibody of the invention, or antigen-binding portion thereof, linked to a therapeutic agent, such as a cytotoxin. The invention also provides a bispecific molecule comprising an antibody, or antigen-binding portion thereof, of the invention, linked to a second functional moiety (e.g., a second antibody) having a different binding specificity than said antibody, or antigen-binding portion thereof. In another aspect, the antibody or an antigen binding portions thereof of the present invention can be made into part of a chimeric antigen receptor (CAR). The antibody or an antigen binding portions thereof of the present invention can also be encoded by or used in conjunction with an oncolytic virus.

Compositions comprising an antibody, or antigen-binding portion thereof, or immunoconjugate, bispecific molecule, or CAR of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-CD40 antibody using the host cell comprising the expression vector is also provided, comprising steps of (i) expressing the antibody in the host cell and (ii) isolating the antibody from the host cell or its cell culture.

In another aspect, the invention provides a method for enhancing an immune response in a subject, comprising administering to the subject a therapeutically effective amount of the antibody, or antigen-binding portion thereof, of the invention. In some embodiments, the method comprises administering a composition, a bispecific molecule, an immunoconjugate, a CAR-T cell, or an antibody-encoding or antibody-bearing oncolytic virus of the invention.

In another aspect, the invention provides a method for treating inflammatory diseases, infectious diseases, atherothrombosis, or respiratory diseases in a subject in need thereof, comprising administering to the subject a therapeutically effective amount of the antibody, or antigen-binding portion thereof, of the invention. In some embodiments, the method comprises administering a composition, a bispecific molecule, an immunoconjugate, a CAR-T cell, or an antibody-encoding or antibody-bearing oncolytic virus of the invention. In some embodiments, additional agents can be administered with the antibody, or an antigen-binding portion thereof, of the invention, such as anti-inflammatory agents and antimicrobial agents. In some embodiments, the inflammatory diseases include autoimmune diseases.

In yet another aspect, the invention provides a method for preventing, treating or ameliorating a cancer disease in a subject, comprising administering to the subject a therapeutically effective amount of the antibody, or antigen-binding portion thereof, of the invention. The cancer may be a solid or non-solid tumor, including, but not limited to, B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer. In some embodiments, the method comprises administering a composition, a bispecific molecule, an immunoconjugate, a CAR-T cell, or an antibody-encoding or antibody-bearing oncolytic virus of the invention. In some embodiments, at least one additional anti-cancer antibody can be administered with the antibody, or an antigen-binding portion thereof, of the invention, such as an anti-VISTA antibody (antibody against the protein V-domain immunoglobulin (Ig) suppressor of T-cell activation (VISTA; programmed death 1 homolog; PD1H; PD-1H)), an anti-PD-1 antibody, an anti-PD-L1 antibody, an anti-LAG-3 antibody and/or an anti-CTLA-4 antibody. In yet another embodiment, an antibody, or an antigen-binding portion thereof, of the invention is administered with a cytokine (e.g., IL-2 and/or IL-21), or a costimulatory antibody (e.g., an anti-CD137 and/or anti-GITR antibody). In another embodiment, an antibody, or an antigen-binding portion thereof, of the invention is administered with a chemotherapeutic agent, which may be a cytotoxic agent, such as epirubicin, oxaliplatin, and/or 5-fluorouracil (5-FU). The antibodies of the present invention can be, for example, mouse, human, chimeric or humanized antibodies.

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIG. 3 shows the agonistic activity of anti-CD40 antibodies.

FIG. 4A-4C show the anti-CD40 antibodies' involvement in dendritic cell maturation as measured by staining of CD86 (A), CD80 (B) and CD83 (C).

FIGS. 9A and 9B show the agonistic activity of chimeric and humanized 7B4 antibodies (A) and chimeric and humanized 13A2 antibodies (B).

FIG. 10A-10C show the anti-CD40 antibodies' involvement in maturation of dendritic cells from donor 1 as measured by staining of CD86 (A), CD80 (B) and CD83 (C).

FIGS. 11A and 11B show the anti-CD40 antibodies' involvement in maturation of dendritic cells from donor 2 as measured by staining of CD86 (A) and CD80 (B).

FIG. 12A-12C show the anti-CD40 antibodies' involvement in maturation of dendritic cells from donor 3 as measured by staining of CD86 (A), CD80 (B) and IL-12 (C).

FIG. 13A-13N show the binding affinity of chimeric and humanized anti-CD40 antibodies 7B4 (A), 7B4-VH0VL0 (B), 7B4-VH2VL2 (C), 7B4-VH2VL3 (D), 7B4-VH3VL2 (E), 7B4-VH3VL3 (F), 13A2 (G), 13A2-VH0VL0 (H), 13A2-VH2VL2 (I), 13A2-VH2VL3 (J), 13A2-VH3VL2 (K) and 13A2-VH3VL3 (L) as well as reference antibodies RO7009789 (M) and ADC1013 (N) to human CD40 as measured by SPR.

FIGS. 16A, 16B and 16C show the engineered anti-CD40 antibodies' involvement in dendritic cell maturation as measured by staining of CD86 (A), CD80 (B) and CD83 (C).

FIGS. 19A and 19B show the in vivo effect of humanized anti-CD40 antibodies on tumor infiltrating CD45+CD3+CD4+ T cell (A) and CD45+CD3+CD8+ T cell (B) proliferation.

FIG. 20 shows the in vivo effect of humanized anti-CD40 antibodies on tumor infiltrating dentritic cell (CD45 positive and CD11c positive cell) maturation as measured by staining of CD86, CD80 and CD83.

DETAILED DESCRIPTION OF THE INVENTION

Figure 1:
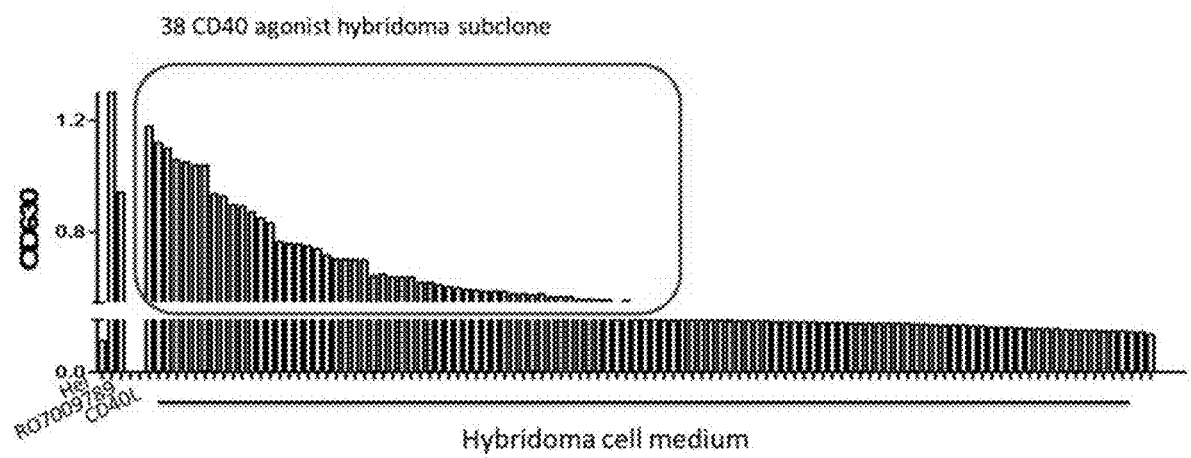
FIG. 1 shows the agonistic activity ranking of 108 hybridoma clones.

To ensure that the present disclosure may be more readily understood, certain terms are first defined. Additional definitions are set forth throughout the detailed description.

The term "CD40" refers to tumor necrosis factor receptor superfamily member 5. The term "CD40" comprises variants, isoforms, homologs, orthologs and paralogs. For example, an antibody specific for a human CD40 protein may, in certain cases, cross-react with a CD40 protein from a species other than human, such as monkey. In other embodiments, an antibody specific for a human CD40 protein may be completely specific for the human CD40 protein and exhibit no cross-reactivity to other species or of other types, or may cross-react with CD40 from certain other species but not all other species.

The term "human CD40" refers to an CD40 protein having an amino acid sequence from a human, such as the amino acid sequence of human CD40 having a Genbank accession number of NP_001241.1 (SEQ ID NO.:68). The terms "monkey or rhesus CD40" and "mouse CD40" refer to monkey and mouse CD40 sequences, respectively, e.g. those with the amino acid sequences having Genbank Accession Nos. NP_001252791.1 (SEQ ID NO.:70) and NP_035741.2 (SEQ ID NO.:72), respectively.

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a CD40 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$ $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and Cm domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a CD40 protein is substantially free of antibodies that specifically bind antigens other than CD40 proteins). An isolated antibody that specifically binds a human CD40 protein may, however, have cross-reactivity to other antigens, such as CD40 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the invention can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human CD40" is intended to refer to an antibody that binds to human CD40 protein (and possibly a CD40 protein from one or more non-human species) but does not substantially bind to non-CD40 proteins. Preferably, the antibody binds to human CD40 protein with "high affinity", namely with a $K_D$ of $5.0 \times 10^{-8}$ M or less, more preferably $1.0 \times 10^{-8}$ M or less, and more preferably $5.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $5.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "agonistic CD40 antibody" or "agonistic anti-CD40 antibody" refers to an anti-CD40 antibody that binds to CD40 and activates or induces CD40 signaling to promote immune cell activation and proliferation as well as cytokine and chemokine production. While the term "antagonistic CD40 antibody" refers to an anti-CD40 antibody that blocks or inhibits CD40 signaling that may be induced by CD40L engagement.

The term "therapeutically effective amount" means an amount of the antibody of the present invention sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

Various aspects of the invention are described in further detail in the following subsections.

Anti-CD40 Antibodies Having Binding Specificity to Human CD40 and Advantageous Functional Properties Antibodies of the invention specifically bind to human CD40 with high affinity, e.g., with a $K_D$ of $1 \times 10^{-8}$ M or less. The antibodies also have cross-reactivity with monkey CD40, but do not bind to mouse CD40.

The antibodies of the invention are agonistic CD40 antibodies that activate or induce CD40 signaling and thus involve in immune cell activation and proliferation as well as cytokine and chemokine production.

The antibodies of the invention have in vivo anti-tumor effect comparable to or better than prior art agnostic anti-CD40 antibodies, with equal or less toxicity. Tumors would not grow or even totally vanish even after antibody administration has stopped.

Preferred antibodies of the invention are monoclonal antibodies. Additionally or alternatively, the antibodies can be, for example, mouse, chimeric or humanized monoclonal antibodies.

Monoclonal Anti-CD40 Antibody

A preferred antibody of the invention is the monoclonal antibody structurally and chemically characterized as described below and in the following Examples. The $V_H$ amino acid sequence of the anti-CD40 antibody is set forth in SEQ ID NOs: 37, 38, 39, 40, 41, 42, 43, 44, 45, 46, 47, 48, 49 or 50. The $V_L$ amino acid sequence of the anti-CD40 antibody is shown in SEQ ID NOs: 51, 52, 53, 54, 55, 56, 57, 58, 59, 60, or 61. The amino acid sequences of the heavy/light chain variable regions of the antibodies are summarized in Table 1 below, some clones sharing the same $V_H$ or $V_L$. Preferable amino acid sequence of the heavy chain constant region for all clones is set forth in SEQ ID NOs: 62, 63 or 64, and preferable amino acid sequence of the light chain constant region for all clones is set forth in SEQ ID NOs: 65 or 66.

The $V_H$ and $V_L$ sequences (or CDR sequences) of other anti-CD40 antibodies which bind to human CD40 can be "mixed and matched" with the $V_H$ and $V_L$ sequences (or CDR sequences) of the anti-CD40 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:

(a) a heavy chain variable region comprising an amino acid sequence listed above in Table 1; and (b) a light chain variable region comprising an amino acid sequence listed above in Table 1, or the $V_L$ of another anti-CD40 antibody, wherein the antibody specifically binds human CD40.

In another embodiment, an antibody of the invention, or an antigen binding portion thereof, comprises:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-CD40 antibody, wherein the antibody specifically binds human CD40.

In yet another embodiment, the antibody, or antigen binding portion thereof, includes the heavy chain variable CDR2 region of anti-CD40 antibody combined with CDRs of other antibodies which bind human CD40, e.g., CDR1 and/or CDR3 from the heavy chain variable region, and/or CDR1, CDR2, and/or CDR3 from the light chain variable region of a different anti-CD40 antibody.

TABLE 1

Amino acid sequences of heavy/light chain variable regions

| Clone/SEQ ID NO. | HV-CDR1 | HV-CDR2 | HV-CDR3 | HV | LV-CDR1 | LV-CDR2 | LV-CDR3 | LV |
|---|---|---|---|---|---|---|---|---|
| 13A2 | 1 | 8 | 15 | 37 | 21 | 27 | 31 | 51 |
| 7B4 | 1 | 9 | 15 | 38 | 21 | 27 | 31 | 52 |
| 16A6 | 2 | 9 | 15 | 39 | 21 | 27 | 31 | 53 |
| 29A10 | 3 | 10 | 16 | 40 | 22 | 28 | 32 | 54 |
| 92F6 | 4 | 11 | 17 | 41 | 23 | 29 | 33 | 55 |
| 77D9 | 5 | 12 | 18 | 42 | 24 | 27 | 34 | 56 |
| 50F6 | 6 | 13 | 19 | 43 | 25 | 27 | 35 | 57 |
| 142F7 | 7 | 14 | 20 | 44 | 26 | 30 | 36 | 58 |
| 13A2-VH0VL0 | 1 | 8 | 15 | 45 | 21 | 27 | 31 | 59 |
| 13A2-VH2VL2 | 1 | 8 | 15 | 46 | 21 | 27 | 31 | 60 |
| 13A2-VH2VL3 | 1 | 8 | 15 | 46 | 21 | 27 | 31 | 61 |
| 13A2-VH3VL2 | 1 | 8 | 15 | 47 | 21 | 27 | 31 | 60 |
| 13A2-VH3VL3 | 1 | 8 | 15 | 47 | 21 | 27 | 31 | 61 |
| 7B4-VH0VL0 | 1 | 9 | 15 | 48 | 21 | 27 | 31 | 59 |

TABLE 1-continued

Amino acid sequences of heavy/light chain variable regions

| Clone/SEQ ID NO. | HV-CDR1 | HV-CDR2 | HV-CDR3 | HV | LV-CDR1 | LV-CDR2 | LV-CDR3 | LV |
|---|---|---|---|---|---|---|---|---|
| 7B4-VH2VL2 | 1 | 9 | 15 | 49 | 21 | 27 | 31 | 60 |
| 7B4-VH2VL3 | 1 | 9 | 15 | 49 | 21 | 27 | 31 | 61 |
| 7B4-VH3VL2 | 1 | 9 | 15 | 50 | 21 | 27 | 31 | 60 |
| 7B4-VH3VL3 | 1 | 9 | 15 | 50 | 21 | 27 | 31 | 61 |

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of the anti-CD40 antibody and at least the CDR3 of the heavy and/or light chain variable region of the anti-CD40 antibody, or the CDR3 of the heavy and/or light chain variable region of another anti-CD40 antibody, wherein the antibody is capable of specifically binding to human CD40. These antibodies preferably (a) compete for binding with CD40; (b) retain the functional characteristics; (c) bind to the same epitope; and/or (d) have a similar binding affinity as the anti-CD40 antibody of the present invention. In yet another embodiment, the antibodies further may comprise the CDR2 of the light chain variable region of the anti-CD40 antibody, or the CDR2 of the light chain variable region of another anti-CD40 antibody, wherein the antibody is capable of specifically binding to human CD40. In another embodiment, the antibodies of the invention may include the CDR1 of the heavy and/or light chain variable region of the anti-CD40 antibody, or the CDR1 of the heavy and/or light chain variable region of another anti-CD40 antibody, wherein the antibody is capable of specifically binding to human CD40.

Conservative Modifications

In another embodiment, an antibody of the invention comprises a heavy and/or light chain variable region sequences of CDR1, CDR2 and CDR3 sequences which differ from those of the anti-CD40 antibodies of the present invention by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and/or conservative modifications thereof; and/or (c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human CD40.

The antibody of the present invention possesses one or more of the following functional properties described above, such as high affinity binding to human CD40, and the ability to induce ADCC or CDC against CD40-expressing cells.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-CD40 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) Nature 332:323-327; Jones et al., (1986) Nature 321:522-525; Queen et al., (1989) Proc. Natl. Acad. See also U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992)J. Mol. Biol. 227:776-798; and Cox et al., (1994) Eur. J. Immunol. 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-CD40 monoclonal antibodies, or antigen binding portions thereof, comprising a heavy chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (0 a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of Cm is modified in such that the number of cysteine residues in the hinge region is altered, e.g., increased or decreased. This approach is described further in U.S. Pat. No. 5,677,425. The number of cysteine residues in the hinge region of Cm is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha$(1,6)-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application corresponding to Alston & Bird LLP, filed on Aug. 11, 2006. PCT Publication WO 99/54342 describes cell lines engineered to express glycoprotein-modifying glycosyl transferases (e.g., $\beta$(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase $\alpha$-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-CD40 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-CD40 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the CD40 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the VL-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-CD40 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Antibody-Encoding or Antibody-Bearing Oncolytic Virus

An oncolytic virus preferentially infects and kills cancer cells. Antibodies of the present invention can be used in conjunction with oncolytic viruses. Alternatively, oncolytic viruses encoding antibodies of the present invention can be introduced into human body.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug, such as anti-VISTA antibody. The pharmaceutical compositions of the invention also can be administered in a combination therapy with, for example, another anti-cancer agent, another anti-inflammatory agent, or an antimicrobial agent.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CD40 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-CD40 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the invention can be formulated to ensure proper distribution in vivo. For example, to ensure that the therapeutic antibody of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS*

*Lett.* 357:140; M. Owais et al., (1995) *Antimicrob. Agents Chemother.* 39:180; Briscoe et al., (1995)*Am. J. Physiol.* 1233:134; Schreier et al., (1994) *J. Biol. Chem.* 269:9090; Keinanen and Laukkanen (1994) *FEBS Lett* 346:123; and Killion and Fidler (1994) *Immunomethods* 4:273.

Uses and Methods of the Invention

Antibodies (compositions, bispecifics, and immunoconjugates) of the present invention have numerous in vitro and in vivo utilities involving, for example, treatment and/or prevention of cancers, inflammatory diseases, or infectious diseases. The antibodies can be administered to human subjects, e.g., in vivo, to inhibit tumor growth.

Given the ability of anti-CD40 antibodies of the invention to inhibit proliferation and survival of cancer cells, the invention provides methods for inhibiting growth of tumor cells in a subject comprising administering to the subject an antibody of the invention such that growth of the tumor is inhibited in the subject. Non-limiting examples of tumors that can be treated by antibodies of the invention include, but not limited to, B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer, original and/or metastatic. Additionally, refractory or recurrent malignancies whose growth may be inhibited using the antibodies of the invention.

In another aspect, the invention provides a method for treating an inflammatory disease, an infectious disease, atherothrombosis, or a respiratory disease in a subject, comprising administering to the subject a therapeutically effective amount of the antibody, or antigen-binding portion thereof, of the invention. Additional anti-inflammatory agents, antimicrobial agents or other therapetical agents can be administered with the antibody, or an antigen-binding portion thereof, of the invention.

Generally speaking, the antibodies of the invention can be used to enhance an immune response in a subject.

These and other methods of the invention are discussed in further detail below.

Combination Therapy

In another aspect, the invention provides methods of combination therapy in which an anti-CD40 antibody (or antigen-binding portion thereof) of the present invention is co-administered with one or more additional antibodies that are effective in inhibiting tumor growth in a subject. In one embodiment, the invention provides a method for inhibiting tumor growth in a subject comprising administering to the subject an anti-CD40 antibody and one or more additional antibodies, such as an anti-VISTA antibody, an anti-LAG-3 antibody, an anti-PD-L1 antibody, and anti-PD-1 antibody and/or an anti-CTLA-4 antibody. In certain embodiments, the subject is human.

The CD40 signaling activation can also be further combined with standard cancer treatments. For example, CD40 signaling activation can be combined with CTLA-4 and/or LAG-3 and/or PD-1 blockade and also chemotherapeutic regimes. For example, a chemotherapeutic agent can be administered with the anti-CD40 antibodies, which may be a cytotoxic agent. For example, epitubicin, oxaliplatin, and 5-FU are administered to patients receiving anti-CD40 therapy.

Optionally, the combination of anti-CD40 and one or more additional antibodies (e.g., anti-CTLA-4 and/or anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

Other therapies that may be combined with anti-CD40 antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Construction of HEK293A Cell Lines Stably Expressing Human, Rhesus or Mouse CD40

Stable cell lines overexpressing human, rhesus or mouse CD40 were constructed using HEK293A cells (Cobioer, N.J., China). Briefly, human, rhesus or mouse CD40 cDNA sequence (SEQ ID NOs: 67, 69 and 71, encoding amino acid sequences set forth in SEQ ID NOs: 68, 70 and 72, respectively) were synthesized, and then subcloned into pLV-EGFP(2A)-Puro vectors. Lentiviruses were generated in HEK-293T cells (Cobioer, N.J., China) by cotransfection of pLV-EGFP(2A)-Puro-CD40, psPAX and pMD2.G plasmids, according to the instruction in Lipofectamine 3000 kit (Thermo Fisher Scientific, US). Three days post cotransfection, the lentiviruses were harvested from the cell culture medium (DMEM medium (Cat #: SH30022.01, Gibco) with 10% FBS (Cat #: FND500, Excell)) of respective HEK-293T cells. Finally, HEK293A cells were infected with the lentiviruses to generate HEK293A cell lines stably expressing human, rhesus or mouse CD40, namely HEK293A/humanCD40, HEK293A/rhesusCD40 or HEK293A/mouseCD40 cells. Transfected HEK293A cells were then cultured in medium (DMEM+10% FBS) containing 0.2 µg/ml puromycin (Cat #: A11138-03, Gibco) for 7 days. The expression of human CD40 and rhesus CD40 were confirmed by FACS using a commercially available anti-human CD40 antibody (PE-anti-human CD40, Biolegend, US, Cat #: 313006). Similarly, the expression of mouse CD40 was confirmed by FACS using a commercially available anti-mouse CD40 antibody (PE-anti-mouse CD40, Biolegend, US, Cat #: 124609).

Example 2 Generation of Hybridoma Cell Lines Producing Monoclonal Mouse Antibodies Against Human CD40

Murine anti-human CD40 monoclonal antibodies (mAbs) were generated using the conventional hybridoma fusion technology with some modifications.

Immunization

Thirteen BALB/c mice (Beijing Vital River Laboratory Animal Technology Co., Ltd, Beijing, China) were injected with recombinant human CD40 (ECD)-his (Sino Biological, CN, Cat #: 10774-H08H) and/or recombinant rhesus CD40 (ECD)-hFc (Sino Biological, CN, Cat #:90097-C02H) following the scheme in Table 2 below. The human CD40 (ECD)-his and rhesus CD40 (ECD)-hFc were emulsified by sonication with an equal volume of Complete Freund's Adjuvant (SIGMA, USA, Cat #: F5881-10*10ML), Incomplete Freund's Adjuvant (SIGMA, USA, Cat #: F5506-6*10ML), or PBS.

monoclonal antibodies binding to human CD40 were further tested for their ability to cross-react with rhesus or mouse CD40.

For ELISA assays, 96-well ELISA plates were coated with 100 μl/well human CD40 (ECD)-his (0.5 μg/ml, Sino Biological, CN, Cat #:10774-H08H), rhesus CD40 (ECD)-hFc (0.5 μg/ml, Sino Biological, CN, Cat #: 90097-C02H) or murine CD40-His (0.5 μg/ml, Sino Biological, CN, Cat #: 50324-M03H) at room temperature overnight. Plates were washed 3 times with PBST buffer (PBS+0.05% Tween 20) and blocked with 200 μl of blocking buffer (PBS containing 1% BSA, 1% goat serum, and 0.05% Tween 20) at RT for

TABLE 2

| Immunization scheme | | | | | |
|---|---|---|---|---|---|
| | Primary | 1st Boost | 2nd Boost | 3rd Boost | Final Boost |
| | | | Day | | |
| | 0 | 14 | 28 | 42 | 56 |
| Protein and dose | Human CD40 (ECD)-his (50 μg/mouse) | Human CD40(ECD)-his (25 μg/mouse) | Human CD40(ECD)-his (25 μg/mouse) + Rhesus CD40(ECD)-hFc (25 μg/mouse) | Human CD40(ECD)-his (25 μg/mouse) + Rhesus CD40(ECD)-hFc (25 μg/mouse) | Human CD40(ECD)-his (50 μg/mouse) |
| Adjuvant | Complete Freund's | Incomplete Freund's | Incomplete Freund's | Incomplete Freund's | PBS |
| Way of immunization | i.p. | s.c. | i.p. | s.c. | i.p. |

One week after each boost, 50 μl of murine serum was collected from each mouse for titer determination by ELISA using the recombinant human CD40 (ECD)-hFc (Sino Biological, CN, Cat #:10774-H02H) and rhesus CD40 (ECD)-hFc (Sino Biological, CN, Cat #: 90097-C02H). Titer determination was also done by FACS using HEK293A overexpressing human CD40, rhesus CD40 or mouse CD40 as prepared in Example 1. Based on the ELISA and FACS analysis results after the final boost, seven mice with highest serum titers were chosen for hybridoma cell line generation.

Generation of Hybridoma Cell Lines

Hybridoma cell lines were generated using the conventional hybridoma fusion technology with minor modifications.

Four days after the final boost, mice were sacrificed, and spleens were collected and prepared as single cell suspensions in PBS. The spleenocytes were washed for three times with DMEM medium (Hyclone, Cat #: SH30243.01B). Viable myeloma cells SP2/0 (ATCC, CRL-1581) at the log-phase were mixed with the murine spleenocytes in a ratio of 1:4. The cells were then washed 2 times and then cell fusion was performed with PEG (Sigma, Cat #: P7181). The post-fusion cells were washed with DMEM medium for three times and suspended in cell growth media (RPMI medium 1640 (Gibco, Cat #:C22400500CP)) supplemented with 10% FBS and 1×HAT (Sigma, H0262). The cell suspension was plated into 96 well cell culture plates, 200 μl per well (5×10$^4$ cells/well), and incubated in a 37° C. humidified 5% CO$_2$ incubator for 7 days. Then, the growth media was replaced by fresh growth media supplemented with 10% FBS+ 1×HT (Sigma, H0137). 2~3 days later, hybridoma cells were screened by ELISA and FACS.

Screening of hybridoma cell lines by ELISA

High-throughput ELISA binding assay was firstly used to screen for hybridoma clones producing monoclonal antibodies binding to human CD40. Hybridoma clones producing 2 hr and washed for 3 times with PBST. Then, hybridoma cell culture supernatant was diluted 10× with dilution buffer (PBS containing 1% BSA, 1% goat serum, and 0.01% Tween 20) and added to the plates, 100 μl per well. After incubated at RT for 1 hr, plates were washed 3 times with PBST and then 100 μl of goat anti-mouse Fc-HRP (1:5000, Sigma, US, Cat #:A9309-1 ml) was added to each well. After incubated at RT for 1 hr, plates were washed 3 times with PBST and then 80 μl of TMB was added to each well. Five to ten minutes later, 80 μl of 0.16 M sulfuric acid was added to each well and then OD450 was read on SpectraMaxR i3X (Molecular Devies, US).

With the ELISA assays, 234 hybridoma clones were identified to have specific binding to both human and rhesus monkey CD40.

Screening of Hybridoma Cell Lines by FACS

The 234 hybridoma clones were further screened for their binding capacity to human, rhesus or mouse CD40 expressed on HEK293A cells. Briefly, 100,000 HEK293A/human CD40 cells, HEK293A/rhesusCD40 cells or HEK293A/mouseCD40 cells as prepared in Example 1 were seeded into each well of the 96-well plates and hybridoma cell culture supernatant diluted 10 times with dilution buffer (PBS plus 1% BSA, 1% goat serum, and 0.01% Tween 20) was added to the plates (100 μl/well). After incubated at 4° C. for 1 hour, plates were washed 3 times with PBST. Then, cells were added with an APC goat anti-mouse IgG (BioLegen, US, Cat #: 405308) diluted 500× was added to the plates. After incubation at 4° C. for 1 hour, plates were washed with PBS for 3 times and then the cell fluorescence was monitored using a FACS machine (BD).

Based on the FACS screening, 162 positive clones were obtained that displayed high binding capacity to both HEK293A/humanCD40 and HEK293A/rhesusCD40 cells.

Subcloning of Hybridoma Clones Producing Anti-CD40 Antibodies

The 162 hybridoma clones were subject to 2 rounds of subcloning. During the subcloning, multiple subclones (n>3) from each parent clone were selected and confirmed by ELISA and FACS assays as described above. The subclones selected through this process were defined as hybridoma cells producing monoclonal antibodies. Finally, 108 subclones (one subclone from each parent clone) having high binding capacity to both human and monkey CD40 were obtained.

Screening of Hybridoma Cell Lines by HEK Blue Activity Assay

The 108 subclones were expanded in 96-well plates and then cultured for 5 days. Supernatants were harvested for HEK-Blue activity assays to identify CD40 antibodies having agonist activity to human CD40.

Briefly, a stable HEK-Blue reporter cell line expressing human CD40 (SEQ ID NO.: 68) (referred to as HEK-Blue/CD40) was established by infecting HEK-Blue null 1_v cells (InvivoGen, San Diego, Calif.) with CD40-expressing lentivirus (which was generated in Example 1), followed by selection with 10 µg/ml puromycin.

For HEK-Blue reporter assay, 40000 HEK-Blue/CD40 cells resuspended in 200 µl of culture media (DMEM medium (Hyclone, USA, Cat #: SH30243.01)+10% FBS (Excell, China, Cat #: FND500)+10 µg/ml Puromycin (GIBCO, USA, Cat #: A11138-03)+100 µg/ml Normocin™ (Invivogen, USA, Cat #: ant-nr-2)+100 µg/ml Zeocin (Invivogen, USA, Cat #: ant-Zn-5)) were plated in a 96-well plate and cultured at 37° C. overnight. On the $2^{nd}$ day, 200 µl of DMEM medium was added to each well to replace the culture medium. Seven hours later, the DMEM medium in the well was replaced with 100 µL/well of HEK Blue Detection buffer (Invitrogen; US; Cat #: hb-det3) and 100 µL/well of hybridoma cell culture supurnatant. The resultant mixtures were incubated at 37° C. under 5% $CO_2$ until the appropriate blue color developed. OD630 was measured using a SpectraMax microplate reader (Molecular Devices; US; SpectraMaxR i3X). An anti-HEL antidbody (LifeTein, LLC, US, Cat. #:LT12031) was used as negative control, and RO7009789 (an agonistic antibody, prepared using amino acid sequences disclosed in U.S. Pat. No. 7,338,660B2 with human IgG2/kappa constant regions) and CD40L (Sino Biological, China, Cat:10239-H08E), the natural ligand and activator of CD40, were used as positive controls. As shown in FIG. 1, 38 clones displayed different levels of CD40 agonist activity while others showed no agonistic activity.

Example 3 Purification of Mouse Anti-CD40 Monoclonal Antibodies

Based on the HEK-Blue assays as mentioned above, 20 clones (see Table 3 below) with high HEK-Blue activity were selected for further characterizations. Monoclonal mouse antibodies from the 20 selected clones were purified. Briefly, hybridoma cells of each subclone were grown in T175 cell culture flasks each having 100 ml of fresh serum-free medium (Gibco, US, Cat #: 12045-076) with 1% HT supplement (Gibco, Cat #: 11067-030). Cell cultures were kept for 10 days in an incubator with 5% $CO_2$ at 37° C. Cell cultures were collected, followed by centrifugation at 3500 rpm for 5 minutes and then subject to filtration using a 0.22 µm capsule to remove the cell debris. Monoclonal mouse antibodies were then purified using a pre-equilibrated Protein-A affinity column (GE, USA, Cat #: 17040501) and eluted with elution buffer (20 mM citric acid, pH3.0-pH3.5). Then, antibodies were kept in PBS buffer (pH 7.0), and their concentrations were determined using a NanoDrop instrument.

The isotype of each purified antibody was determined by using the Rapid Isotyping Kit with Kappa and Lambda-Mouse (Thermal, USA, Cat #: 26179) and Mouse Monoclonal Antibody Isotyping Reagents (Sigma, USA, Cat #: IS02-1KT), following the manufacturer's manuals. The isotyping results and the expression titer of the selected top 20 clones were summarized in Table 3.

TABLE 3

Isotype and expression titer of anti-OD40 antibodies

| clone | Isotype | Expression titer (mg/L) |
|---|---|---|
| 13A2 | mouse IgGl/κ | 24.744 |
| 16A6 | mouse IgGl/κ | 31.111 |
| 29A10 | mouse IgGl/κ | 33.889 |
| 7B4 | mouse IgGl/κ | 18.667 |
| 9A7 | mouse IgGl/κ | 7.778 |
| 19H4 | mouse IgGl/κ | 10.000 |
| 37G10 | mouse IgGl/κ | 65.333 |
| 35C9 | mouse IgGl/κ | 11.667 |
| 16F4 | mouse IgG2b/κ | 14.000 |
| 50F6 | mouse IgGl/κ | 12.778 |
| 77D9 | mouse IgGl/κ | 12.22 |
| 79D7 | mouse IgGl/κ | 20.39 |
| 142F7 | mouse IgGl/κ | 17.22 |
| 89D11 | mouse IgGl/κ | 95.73 |
| 91E4 | mouse IgG2a/κ | 4.47 |
| 101C12 | mouse IgGl/κ | 18.94 |
| 92F6 | mouse IgGl/κ | 39.97 |
| 82D3 | mouse IgG2a/κ | 16.27 |
| 23B8 | mouse IgG2a/κ | 32.33 |
| 51F7 | mouse IgGl/κ | 1.44 |

Example 4 Purified Mouse Anti-CD40 Monoclonal Antibodies Bound to Human and Monkey CD40

Purified mouse anti-CD40 monoclonal antibodies were firstly characterized by ELISA assays to determine their binding affinities to recombinant human, monkey or mouse CD40 proteins.

ELISA plates were coated with 500 ng/ml human CD40 (ECD)-his (Sino Biological, CN, Cat #: 10774-H08H) at 4° C. overnight. The wells were blocked with 200 µl of blocking buffer (PBS containing 1% BSA, 1% goat serum, and 0.05% Tween 20) for 2 hours at room temperature, and then 100 µl of serially diluted anti-CD40 antibodies (starting from 40000 ng/ml) were added to each well and incubated for 1 hour at RT. Plates were washed for 3 times with PBST (PBS+0.05% Tween 20), added with Goat-anti-mouse IgG-HRP (Simga, US, Cat #: A9309-1 ml) diluted 5000×, and incubated for 1 hour at RT. Plates were developed with freshly prepared Ultra-TMB (BD, US, Cat #:555214) for 5 minutes at RT. Absorbance was read on a SpectraMax® i3X (Molecular Devies, US) at 450 nm.

Species-cross-reactivity of the 20 CD40 mAbs to monkey or mouse CD40 was further assessed by direct ELISA. Briefly, 500 ng/ml monkey CD40 (ECD)-hFc (Sino Biological, CN, Cat #: 90097-C02H) or mouse CD40-hFc (Sino Biological, CN, Cat #: 50324-M03H) was coated on 96-well ELISA plates followed by incubation with 100 µl of serially diluted anti-CD40 antibodies (starting from 40000 ng/ml). Goat anti-mouse IgG conjugated with HRP (Sigma, US, Cat #:A9309-1 ml) was used then. Anti-CD40 antibodies RO7009789 and ADC1013 (prepared using the amino acid sequences disclosed in US2016/0311916A1 with human IgG1/kappa constant regions) were used as references.

$EC_{50}$ values for these binding tests were summarized in Table 4. It can be seen that all the 20 antibodies, except 51F7, clearly cross-reacted with monkey CD40 but not with mouse CD40.

TABLE 4

Binding capacity of 20 mouse anti-CD40 mAbs to human, monkey or mouse CD40

| Clone | ELISA ($EC_{50}$: ng/ml) | | |
|---|---|---|---|
| | hCD40 (ECD)-his | rhCD40 (ECd)-hFc | muCD40-hFc |
| RO7009789 | 20.65 | 16.16 | N/A |
| ADC1013 | 24.03 | 22.92 | N/A |
| 9A7 | 17.39 | 1349 | N/A |
| 16A6 | 13.12 | 12.95 | N/A |
| 19H4 | 26.09 | 20.46 | N/A |
| 29A10 | 31.82 | 30.21 | N/A |
| 16F4 | 25.68 | 23.38 | N/A |
| 35C9 | 21.64 | 21.33 | N/A |
| 50F6 | 15.52 | 16.02 | N/A |
| 7B4 | 15.29 | 15.25 | N/A |
| 13A2 | 20.65 | 14.08 | N/A |
| 37G3 | 24.03 | 30.15 | N/A |
| 77D9 | 21.37 | 20.56 | N/A |
| 79D7 | 15.64 | 17.02 | N/A |
| 142F7 | 17.12 | 20.14 | N/A |
| 89D11 | 156.7 | 142.7 | N/A |
| 91E4 | 17.68 | 18.87 | N/A |
| 101C12 | 19.09 | 19.77 | N/A |
| 92F6 | 29.11 | 36.55 | N/A |
| 82D3 | 15.26 | 17.64 | N/A |
| 23B8 | 17.76 | 18.42 | N/A |
| 51F7 | 47.87 | N/A | N/A |

Example 5 Mouse Anti-CD40 Monoclonal Antibodies Bound to Human and Rhesus CD40 Expressed on HEK293A Cells To further determine whether anti-CD40 antibodies bound to human, monkey or mouse CD40 expressed on HEK293A cells, a cell-based binding assay by FACS was performed using the HEK293A cells stably overexpressing human, monkey or mouse CD40 as generated in Example 1, respectively. Briefly, $10^5$ HEK293A cells were seeded into each well of the 96-well plates and serially diluted anti-CD40 antibodies were added to the plates. After incubated at 4° C. for 1 hour, plates were washed 3 times with PBST. Then, an APC coupled Goat Anti-Mouse IgG (BioLegen, US, Cat #:405308) diluted 500× was added to the plates. After incubation at 4° C. for 1 hour, the plates were washed with PBS for 3 times and then cell fluorescence was monitored using a FACS machine (BD).

As shown in Table 5 below, all of the mouse anti-CD40 monoclonal antibodies showed high binding capacity to both human and rhesus monkey CD40 but did not bind to mouse CD40 (data not shown).

TABLE 5

Binding affinity of mouse anti OX-40 antibodies to human and monkey CD40

| Clone | FACS($EC_{50}$: ng/ml) | |
|---|---|---|
| | HEK-293A/h CD40 | HEK-293A/Rh CD40 |
| RO7009789 | 227.4 | 184.8 |
| ADC1013 | 148.7 | 67.29 |
| 9A7 | 90.53 | 6876 |
| 16A6 | 68.21 | 44.03 |
| 19H4 | 227.7 | 206.6 |
| 29A10 | 202.6 | 184.5 |
| 16F4 | 199.5 | 125.7 |
| 35C9 | 181.8 | 172 |
| 50F6 | 134.1 | 136.6 |
| 7B4 | 10.09 | 15.87 |
| 13A2 | 48.45 | 84.27 |
| 37G3 | 203.2 | 185.6 |
| 77D9 | 33.03 | 117.2 |
| 79D7 | 12.35 | 78.42 |
| 142F7 | 15.46 | 80.66 |
| 89D11 | 58.03 | 83.58 |
| 91E4 | 48.66 | 101.8 |
| 101C12 | 21.87 | 62.63 |
| 92F6 | 77.86 | 129.6 |
| 82D3 | 21.77 | 130.7 |
| 23B8 | 1029 | 1034 |
| 51F7 | 108.6 | 483.8 |

Example 6 Mouse Anti-CD40 Antibodies Inhibited or Promoted Human CD40-CD40L Interaction Purified anti-CD40 antibodies were further analyzed for their ability of blocking or promoting binding of human CD40L to human CD40. Briefly, 96-well ELISA plates were coated with 500 ng/ml human CD40L (Sino Biological, China, Cat:10239-H08E) at 4° C. overnight. The plates were blocked with 200 µl of blocking buffer (PBS+2% BSA) for 2 hours at room temperature. Then serially diluted anti-CD40 antibodies (starting from 40 µg/ml) were mixed and incubated with 2 µg/ml human CD40-hFc (Sino biological, Cat #:10774-H02H) at 37° C. for 1 hour, which mixtures were then added into the wells and incubated at RT for 1 hour. The plates were washed 3 times with PBST (PBS+ 0.05% Tween20), added with anti-Human IgG FC-HRP (1:5000, Sigma, USA, Cat #: A0170-1ML), and then incubated at room temperature for 1 hour. Plates were washed 3 times with PBST and then 80 µl of TMB was added to each well. Five to ten min later, 80 µl of 0.16 M sulfuric acid was added to each well and then OD450 was measured on a SpectraMaxR i3X (Molecular Devies, US).

Figure 2A:
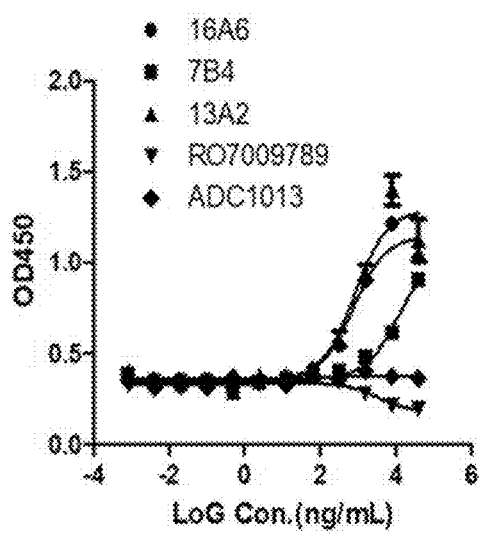
FIGS. 2A and 2B show the promotional or inhibitory effect of anti-CD40 antibodies on CD40/CD40L interaction, wherein antibodies 16A, 7B4 and 13A promoted CD40/CD40L interaction (A) while antibody 92F6 inhibited CD40/CD40L interaction (B).
Figure 2B:
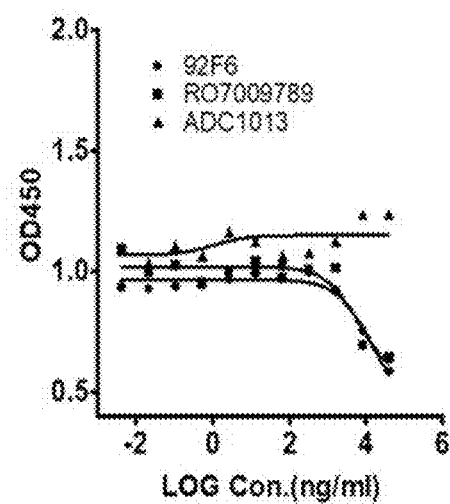

Interestingly, the data showed that 6 mouse antibodies (13A2, 16A6, 7B4, 50F6, 142F7 and 101C12) promoted the human CD40/CD40L interactions while another 3 antibodies (23B8, 92F6, 82D3) blocked the CD40-CD40L interactions, with the remainings having no evident influence on CD40-CD40L interaction. Results of 4 representative antibodies were shown in FIGS. 2A and 2B.

Example 7 Determination of Agonistic Activity of Mouse Anti-CD40 Antibodies

To determine whether the selected mouse anti-CD40 antibodies had agonistic activity, a HEK-Blue activity assay was performed. Briefly, the HEK-Blue/CD40 cells, generated in Example 2, were incubated in DMEM medium (Hyclone, USA, Cat #: SH30243.01)+10% FBS (Excell, China, Cat #: FND500)+10 µg/ml Puromycin (GIBCO, USA, Cat #: A11138-03)+100 µg/ml Normocin™ (Invivogen, USA, Cat #: ant-nr-2)+100 µg/ml Zeocin (Invivogen, USA, Cat #: ant-Zn-5). Forty-thousand (40,000) HEK-Blue/ CD40 cells in 200 µl of culture medium were aliquoted in each well of the 96-well assay plate and cultured at 37° C. After overnight incubation (~12 hour), 200 µl of fresh DMEM medium was used to replace the culture medium. Seven hours later, the DMEM medium in each well was replaced with 100 µL/well of HEK Blue Detection buffer (Invivogen; USA; Cat #: hb-det3) containing anti-CD40 antibodies at various concentration (from 100 µg/ml to 0.01 ng/ml). The cells were incubated at 37° C. until appropriate blue color developed. Absorbence at 630 nm was measured using a SpectraMax microplate reader (Molecular Devices, US, SpectraMaxR i3x).

$EC_{50}$ values were summarized in Table 6 below, and representative curves were shown in FIG. 3. As can be seen, all 20 mouse antibodies displayed different agonist activities in the HEK-Blue assay, suggesting their abilities in simulating CD40 downstream signalings.

TABLE 6

Agonistic activity of anti-CD40 antibodies

| Antibody | HEK Blue $EC_{50}$(ng/mL) |
| --- | --- |
| RO7009789 | 23.26 |
| ADC1013 | 1034 |
| 13A2 | 12.61 |
| 16A6 | 11.37 |
| 7B4 | 26.14 |
| 50F6 | 42.16 |
| 101C12 | 175.2 |
| 77D9 | 22.26 |
| 35C9 | 86.08 |
| 37G3 | 146.1 |
| 79D7 | 55.29 |
| 142F7 | 64.77 |
| 89D11 | 91.06 |
| 91E4 | 152.7 |
| 82D3 | 285.4 |
| 23B8 | 3373 |
| 51F7 | 6173 |
| 92F6 | 263.7 |
| 19H4 | 92.79 |
| 16F4 | 252.1 |
| 29A10 | 139.8 |
| 9A7 | 61.96 |

Example 8 Epitope Binning

For epitope binning, a competition ELISA assay was performed. Briefly, 96-well plates were coated with 5 µg/ml RO7009789 or ADC1013 at 4° C. overnight. The wells were blocked with 200 µl of blocking buffer (PBS containing 1% BSA, 1% goat serum, and 0.05% Tween 20) for 2 hours at room temperature. Human CD40 (ECD)-His (Sino Biological, CN, Cat #:10774-H08H) was diluted to 0.5 µg/mL and added to the plate which was then incubated for 1 hour at RT. The ELISA plates were washed for 3 times with PBST, and then the purified antibodies were diluted to 1 µg/mL and added to each well and allowed to incubate for 1 hour at RT. The ELISA plates were washed for 3 times with PBST, and then anti-mouse Fc-HRP (Sigma, US, Cat #: A9309-1MC) diluted at 1:20000 was added to each well and incubated for 1 hour at RT. Plates were developed with freshly prepared Ultra-TMB (Huzhou Yingchuang, CN, Cat #: TMB-S-003) for 5 minutes at RT and the absorbance was measured on SpectraMax microplate reader (Molecular Devices; US; SpectraMaxR i3x) at 450 nm (OD450).

The results were summarized in Table 7. Seven mouse antibodies (101C12, 142F7, 89D11, 13A2, 16A6, 7B4 and 50F6) competed with both reference antibodies while antibodies 9A7, 92F6, 19H4, 16F4 and 51F7 did not show competition with either reference antibody. The remaining antibodies competed with either of the two reference antibodies.

TABLE 7

Epitope binning by competition ELISA

| | Binning results | |
| --- | --- | --- |
| Antibodies | R07009789 | ADC1013 |
| 13A2 | + | + |
| 16A6 | + | + |
| 7B4 | + | + |
| 50F6 | + | + |
| 101C12 | + | + |
| 77D9 | + | − |
| 35C9 | + | − |
| 37G3 | + | − |
| 29A10 | + | − |
| 9A7 | − | − |
| 92F6 | − | − |
| 19H4 | − | − |
| 16F4 | − | − |
| 79D7 | − | − |
| 142F7 | + | + |
| 89D11 | + | + |
| 91E4 | + | − |
| 82D3 | + | − |
| 23B8 | + | − |
| 51F7 | − | − |

+: with competition;
−: without competition

Example 9 Agonistic Anti-CD40 Antibodies Drove Dendritic Cell Maturation

To further determine the agonistic activity of the mouse anti-CD40 antibodies, a dendritic cell maturation assay was performed. Briefly, PBMCs from one healthy human donor's blood sample were collected by density gradient centrifugation and then resuspended in RPMI1640 medium. PBMCs were cultured n a 37° C. incubator for 2 hours, and cells adhered to container walls were collected as isolated monocytes. The monocytes were cultured with 100 ng/ml of recombinant human GM-CSF (R&D, US, Cat #: 7954-GM) and 100 ng/ml of recombinant human IL-4 (R&D, US, Cat #: 6507-IL) in RPMI1640 media supplemented with 10% FBS in a 24-well plate. Three days later, half of the medium was replaced with fresh medium. On day 6 of culturing, anti-CD40 antibodies (10 µg/ml or 1 µg/ml), or the control antibodies (RO7009789, ADC1013 and Hel (LifeTein, US, Cat #: LT12031)) were added to the cells, and the plate was further cultured for 48 h. FITC Mouse Anti-human CD83 (BD, USA, Cat #: 556910), PE Mouse Anti-human CD86 (BD, Cat #: 555658), and BV650 Mouse Anti-human CD80 (BD, USA, Cat #: 564158) were used for staining of DC activation markers by FACS.

Results of representative antibodies were shown in FIG. 4A-4C. Mouse anti-CD40 antibodies 16A6, 29A10, 7B4 and 13A2 increased the expression of CD86, a biomarker of maturated dendritic cells, as compared to anti-Hel isotype control, and antibodies 16A6, 29A10, 7B4 and 13A2 significantly up-regulated expression of CD80 and CD83, both being co-stimulatory molecules.

Example 10 Expression and Purification of Chimeric Anti-CD40 Antibodies

Eight antibodies (13A2, 16A6, 7B4, 29A10, 92F6, 77D9, 50F6 and 142F7) were selected for further tests. The variable region sequences of the 8 selected candidate antibodies were cloned from hybridoma cells using the standard PCR method with a set of degenerated primers as describes in literatures (Juste et al., (2006), Anal Biochem. 1; 349(1): 159-61). Expression vectors were constructed by inserting the sequences encoding the variable region sequences plus respective human IgG2/kappa constant region sequences (amino acid sequences of heavy chain constant region and light chain constant region set forth in SEQ ID NOs: 63 and 65, respectively) into XhoI/BamHI restriction sites of pCDNA3.1 (Invitrogen, Carlsbad, USA). The amino acid SEQ ID numbers of variable regions were summarized in Table 1 above.

The expression vectors were PEI transfected into HEK-293F cells (Cobioer, N.J., China). In specific, HEK-293F cells were cultured in Free Style™ 293 Expression Medium (Gibco, Cat #: 12338-018) and transfected with the expression vectors using polyethyleneinimine (PEI) at a DNA:PEI ratio of 1:3, 1.5 µg of DNAs per millimeter of cell medium. Transfected HEK-293F cells were cultured in an incubator at 37° C. under 5% $CO_2$ with shaking at 120 RPM. After 10-12 days, supernatants were harvested and monoclonal antibodies were purified as described in Example 3.

Example 11 Chimeric Anti-CD40 Monoclonal Antibodies Bound to Human or Rhesus Monkey CD40 Expressed on HEK293A Cells The chimeric anti-CD40 antibodies were further characterized for their ability of binding to HEK293A/humanCD40 cells, HEK293A/rhesusCD40 cells and HEK293A/mouseCD40 cells as generated in Example 1, according to the protocol of Example 5.

Figure 5A:
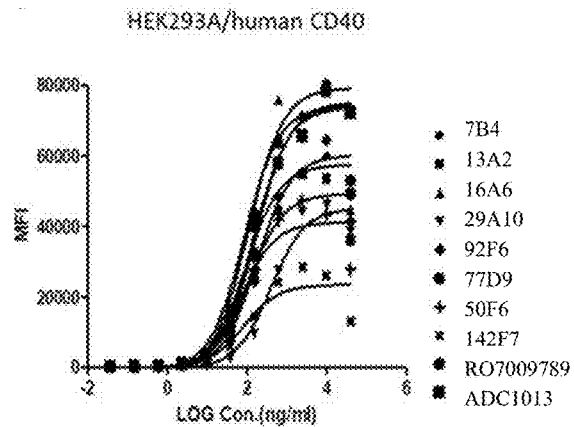
FIGS. 5A and 5B show the binding capacity of the chimeric anti-CD40 antibodies to human CD 40 (A) or monkey CD40 (B) expressed on HEK293A cells.
Figure 5B:
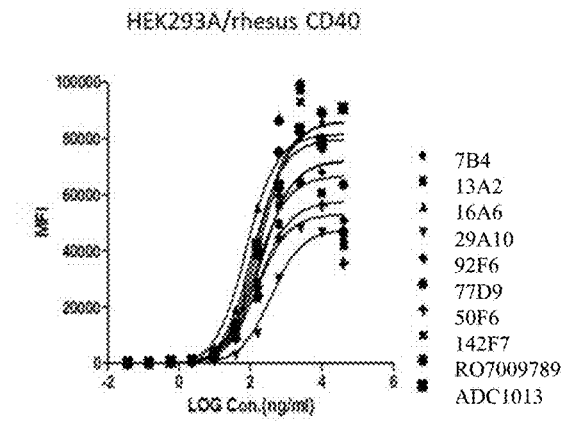

As shown in FIGS. 5A and 5B, the chimeric antibodies had high binding affinity to both human and monkey CD40. These chimeric antibodies did not bind to mouse CD40 (data not shown).

Example 12 Chimeric Anti-CD40 Monoclonal Antibodies had Angonist Activity and Drove Dendritic Cell Maturation The chimeric antibodies were assayed for their effect on CD40 signaling activation by HEK-Blue assay and dendritic cell maturation assay, following the protocols described in Example 7 and Example 9. RO7009789, APX005 (prepared using the amino acid sequences disclosed in WO2014/070934A1 having human IgG1/kappa constant regions) and/or ADC1013 were used as references.

Figure 6:
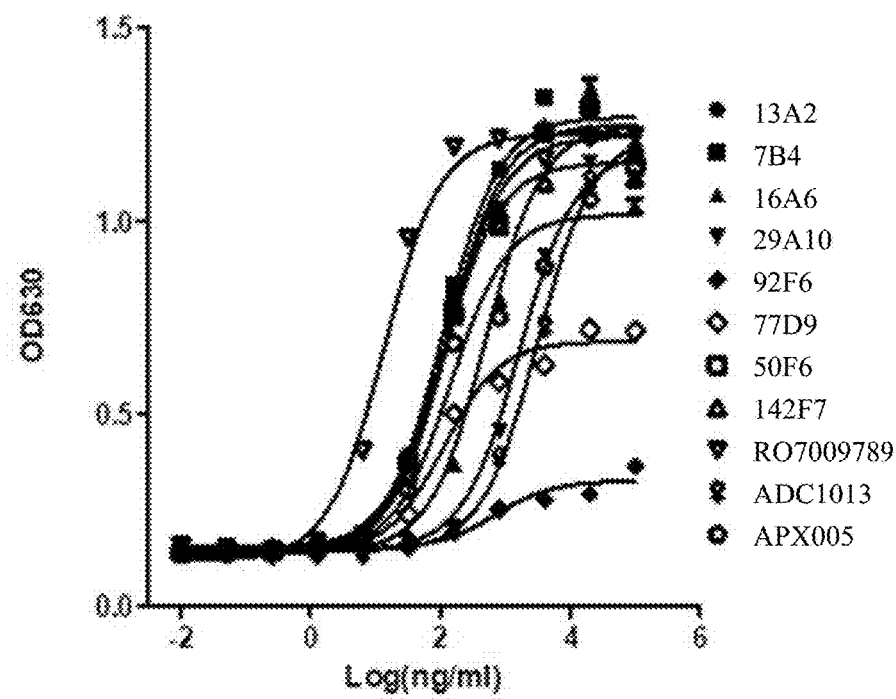
FIG. 6 shows the agonistic activity of the chimeric anti-CD40 antibodies.
Figure 7:
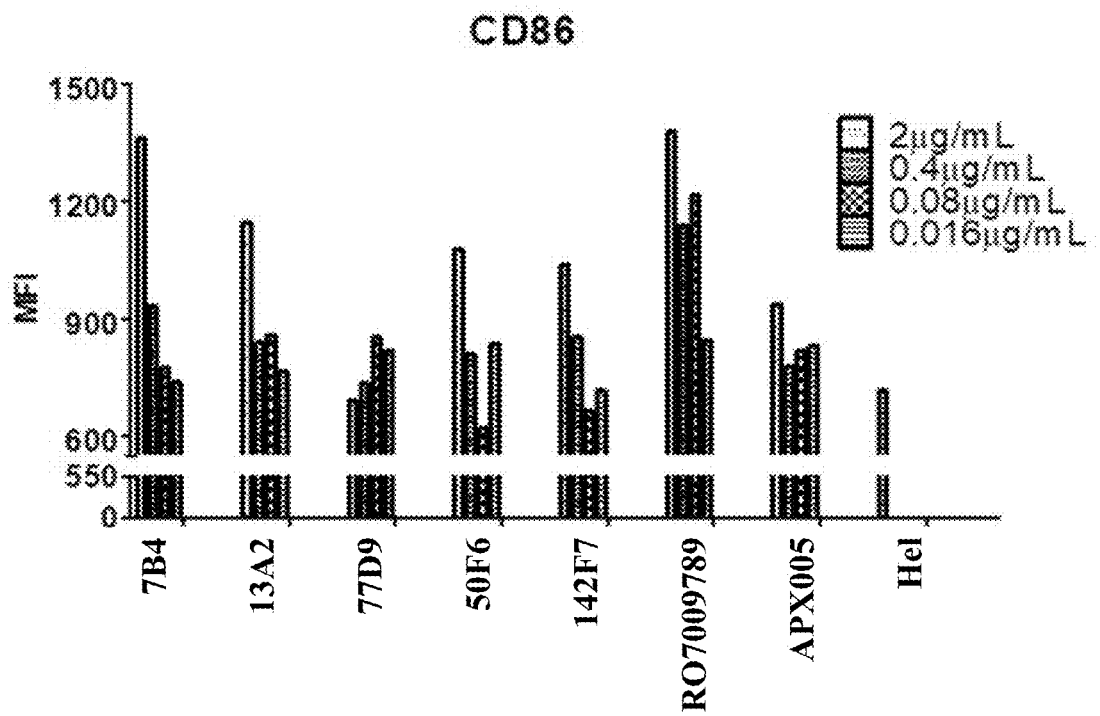
FIG. 7 shows the anti-CD40 antibodies' involvement in dendritic cell maturation as measured by staining of CD86.
Figures 8A, 8B:
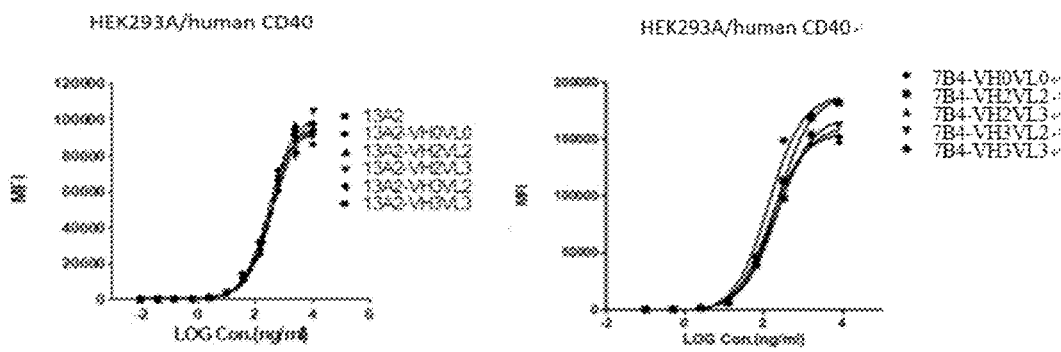
FIG. 8A-8D show the binding capacity of chimeric and humanized anti-CD40 antibodies to human, or monkey CD40, wherein chimeric and humanized 13A2 antibodies (A) and humanized 7B4 antibodies (B) bound to human CD40, and chimeric and humanized 13A2 antibodies (C) and humanized 7B4 antibodies (D) bound to monkey CD40.
Figures 8C, 8D:
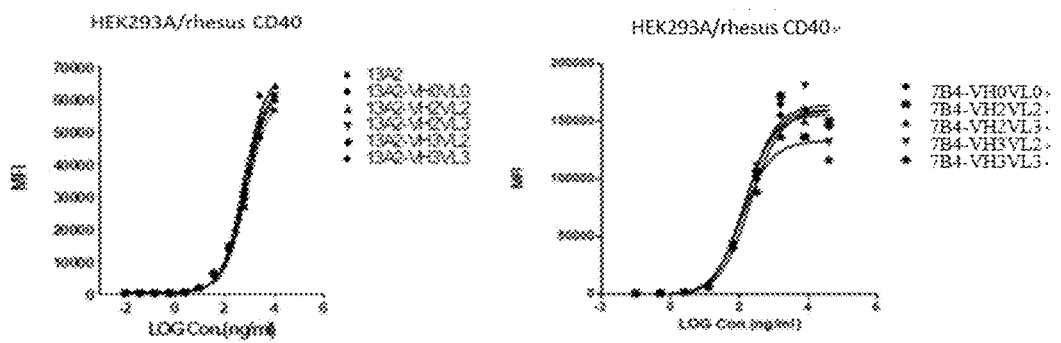

As shown in FIG. 6, the 8 chimeric antibodies displayed similar functional activities as their parent monoclonal antibodies. FIG. 7 showed that all tested chimeric antibodies drove maturation of dendritic cells, as suggested by upregulation of CD86, the biomark of maturated dendritic cells.

Example 13 Humanization of Anti-CD40 Antibodies

Based on the characterizations and assays described above, two candidate antibodies, 7B4 and 13A2, were selected for humanization and further investigations. Humanization of the murine antibodies was conducted using the well-established CDR-grafting method (U.S. Pat. No. 5,225,539, incorporated herein by reference in its entirety) as described in detail below.

To select acceptor frameworks for humanization of murine antibodies 7B4 and 13A2, the light and heavy chain variable region sequences of 7B4 and 13A2 were blasted against the human immunoglobulin gene database in NCBI website (http://www.ncbi.nlm.nih.gov/igblast/). The human germline IGVH and IGVK with the highest homology to 7B4 and 13A2 were selected as the acceptor for humanization. For antibodies 7B4 and 13A2, the human heavy chain acceptor selected was IGHV4-28*06, and the human light chain acceptor selected was IGKV2-30*02 listed in Table 8 below.

The three dimensional structures were simulated for variable domains of 7B4 and 13A2 in order to identify key framework residues that might be playing important roles in supporting CDR loop structures, thus designing back mutations in humanized antibodies. Selected structure templates had the same classes of canonical loop structures in L-CDR1, L-CDR2, L-CDR3, H-CDR1, H-CDR2 and H-CDR3 to 7B4 and 13A2, respectively. Using the structural templates selected, structural models were built by replacing the murine frameworks with human acceptor's frameworks for heavy and light chains. Three-dimensional structural modeling simulation was then performed to identify key framework residues that might be important in supporting the CDR-loop structures or the heavy and light chain interface. When the murine antibody and the human acceptor shared the same residue at a certain site in the framework, the human germline residue was kept. On the other hand, when the murine antibody and human germline acceptor had a different residue at a certain site in the framework, the importance of this residue was evaluated by structural modeling. If a residue in the murine antibody's framework was found to interact with and influence the CDR residues, then this residue was back-mutated to murine residue.

TABLE 8

Structural templates used in antibody structure simulations

| Antibody chain | PDB code of template structure | Sequence identity | Sequence similarity |
|---|---|---|---|
| 13A2 Heavy chain | 5E2T | 71% | 83% |
| 13A2 Light chain | 1DLF | 84% | 92% |
| 7B4 Heavy chain | 5E2T | 87% | 90% |
| 7B4 Light chain | 1DLF | 87% | 95% |

Based on the structural modeling as described above, 5 potential back-mutations (I49M, V68I, M70I, K44N, G45K) were identified for heavy chain and 5 potential back-mutations (M4L, R51L, F76L, Y92F, Q105S) for light chain of 13A2. For 7B4, 5 potential back-mutations (I49M, V68I, M70I, K44N, G45K) were identified for heavy chain and 4 back-mutations (M4L, R51L, Y92F, Q105S) were identified for light chain.

As summarized in Table 1, for both 7B4 and 13A2, three humanized heavy chain variable regions and three humanized light chain variable regions were designed, with a total of 5 humanized antibodies.

The sequences encoding the humanized heavy chain variable region plus human IgG2 constant region, and the sequence encoding light chain variable regions plus human kappa constant region (amino acid sequences of heavy chain constant region and light chain constant region set forth in SEQ ID NOs: 63 and 65, respectively) were chemically synthesized and then subcloned into the pcDNA3.1(+)-based expression vector (Invitrogen, USA) using the BamH I and Xho I restriction sites, respectively. All expression constructs were confirmed by DNA sequencing. The HEK293F expression systems (Invitrogen, USA) were transfected with heavy chain and light chain expressing vectors and transiently expressed 10 humanized anti-CD40 antibodies (5 for 13A2, and 5 for 7B4), according to the protocol described in Example 10. The humanized antibodies were purified as described in Example 3.

Example 14 Characterization of Chimeric and Humanized Anti-CD40 Antibodies

The chimeric and humanized anti-CD40 antibodies were further characterized for their ability of binding to HEK293A/humanCD40 cells and HEK293A/rhesus CD40 cells, following the protocols described in Example 5. They were also tested for their ability to activate CD40 signaling in HEK-Blue assay, and to promote dendritic cell maturation, following the protocols in Example 7 and Example 9, respectively, the dendritic cells collected form three healthy human donors. IL-12(p40) secretion by the dendritic cells was measured by using human IL12(p40) ELISA kit (BD, US, Cat #:551116) following themanufactor's instruction.

As shown in FIG. 8A-8D, FIG. 9A-9B, FIG. 10A-10C (Donor 1), FIG. 11A-11B (Donor 2), and FIG. 12A-12C (Donor 3), the humanized anti-CD40 antibodies 13A2-$V_H3V_L2$, 13A2-$V_H3V_L3$, and 7B4H2L2 showed best binding, agonistic and functional activities.

Example 15 Affinity of Chimeric or Humanized Anti-CD40 Antibodies to Human CD40

SPR assays were used to determine the binding affinity of the chimetic or humanized anti-CD40 antibodies to human CD40 with the BIAcore™ 8K instrument (GE Life Sciences). Briefly, 100-200 response units (RU) of human CD40 (ECD)-his protein (Sino Biological, CN, Cat #:10774-H08H) were coupled to CM5 biosensor chips (Cat #: BR-1005-30, GE Life Sciences), followed by blocking of un-reacted groups with 1M ethanolamine. Serially diluted antibodies at concentrations ranging from 0.3 µM to 10 µM were injected into the SPR running buffer (HBS-EP buffer, pH7.4, GE Life Sciences; US; Cat #:BR-1006-69) at 30 4/minute. The binding capacity was calculated with the RUs of blank controls subtracted. The association rate ($k_a$) and dissociation rate ($k_d$) were calculated using the one-to-one Langmuir binding model (BIA Evaluation Software, GE Life Sciences). The equilibrium dissociation constant $K_D$ was calculated as the $k_d/k_a$ ratio. The SPR-determined binding curves of antibodies were shown in FIGS. 13A-13N, and the binding affinities of those chimeric or humanized antibodies were listed in Table 9.

TABLE 9

Binding affinities of anti-CD40 antibodies to human CD40

| Antibodies | $k_a$ | $k_d$ | $K_D$ |
|---|---|---|---|
| RO700789 | 1.07E+5 | 1.83E−4 | 1.71E−9 |
| ADC1013 | 1.2E+6 | 3.48E−2 | 2.9E−8 |
| 13A2 | 4.84E+05 | 1.73E−03 | 3.58E−09 |
| 13A2-VH0VL0 | 3.96E+05 | 1.14E−02 | 2.88E−08 |
| 13A2-VH2VL2 | 8.23E+05 | 1.71E−03 | 2.08E−09 |
| 13A2-VH2VL3 | 7.35E+05 | 2.61E−03 | 3.55E−09 |
| 13A2-VH3VL2 | 8.25E+5 | 2.42E−3 | 2.93E−9 |
| 13A2-VH3VL3 | 5.98E+5 | 4.59E−3 | 7.68E−9 |
| 7B4 | 1.00E+06 | 3.6E−03 | 3.6E−09 |
| 7B4-VH0VL0 | 2.75E+06 | 6.8E−03 | 2.47E−09 |
| 7B4-VH2VL2 | 2E+06 | 5.81E−03 | 2.91E−09 |
| 7B4-VH2VL3 | 1.78E+06 | 6.39E−03 | 3.6E−09 |
| 7B4-VH3VL2 | 1.46E+06 | 6.15E−03 | 4.2E−09 |
| 7B4-VH3VL3 | 2.13E+06 | 4.88E−03 | 2.99E−09 |

Example 16 Epitope Mapping of Chimeric or Humanized Anti-CD40 Antibodies

The chimeric and humanized anti-CD40 antibodies were tested for their binding epitope by ELISA.

There are four individual cysteine enriched domains (CRD) in CD40 extracellular domain (ECD), namely CRD1, CRD2, CRD3 and CRD4. Based on the structure of CD40 ECD, one full-length CD40 ECD, five CD40 ECD truncants and four CD40 ECD mutants were generated, and their information can be found in Table 10 below. These recombinant proteins were linked with a signal peptide (SEQ ID NO.: 83) at the N terminus for protein secretion and a mFc-tag (SEQ ID NO.: 84) at the C terminus for ELISA assay. DNA sequences encoding these recombinant proteins were synthesized and subcloned into pcDNA3.1 vector. The expression and purification of the recombinant proteins were carried out according to the protocols in Example 10. ELISA assay was performed to assess binding capacity of mAbs to recombinant CD40 proteins, following the protocol in Example 2.

Figure 14A:
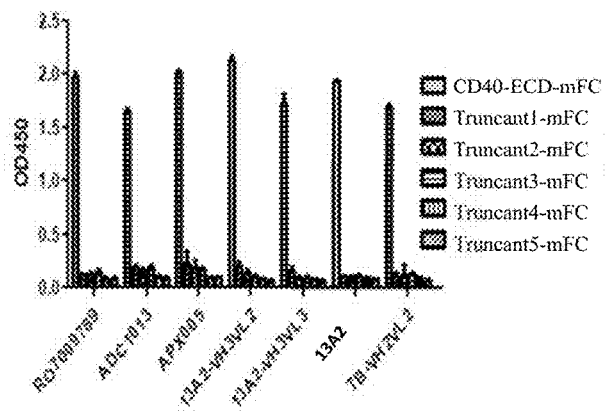
FIGS. 14A and 14B show the binding capacity of chimeric and humanized anti-CD40 antibodies to full-length CD40-ECD or its truncants (A) and to full-length CD40-ECD or its mutants (B).
Figure 14B:
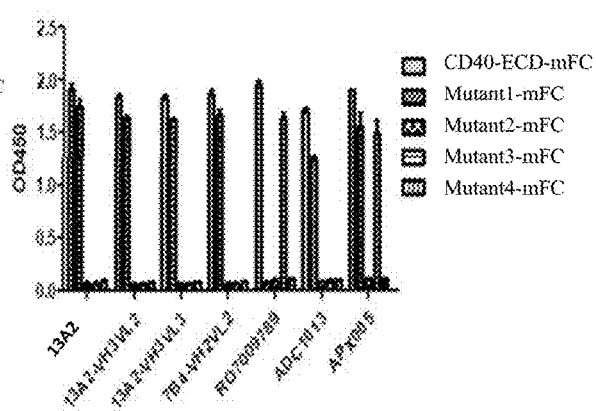

As shown in FIG. 14A, all the antibodies bound to full-length CD40 ECD, but none of them bound to the truncants, indicating CRD1 domain of CD40 was involved in and important to the binding of antibodies. FIG. 14B showed that the chimeric 13A2 antibody, the three humanized antibodies and ADC1013 cannot bind to CD40 Mutant 2-4, indicating the five antibodies shared the same or similar binding epitope. RO7009789 cannot bind to Mutant 1, 2 and 4 while APX005 cannot bind to Mutant 2 and 4.

TABLE 10

CD40 ECD truncants and mutants

| CD40 ECD recombinant protein | SEQ ID NO. | CRD | Mutation |
|---|---|---|---|
| Full-length CD40 ECD (amino acid 21-193, human CD40) | 73 | CRD1/2/3/4 | n/a |
| Truncant 1 (amino acid 61-193) | 74 | CRD2/3/4 | n/a |
| Truncant 2 (amino acid 104-193) | 75 | CRD3/4 | n/a |
| Truncant 3 (amino acid 145-193) | 76 | CRD4 | n/a |
| Truncant 4 (amino acid 38-193) | 77 | CRDΔ1/2/3/4 | n/a |
| Truncant 5 (amino acid 21-37 & 61-193) | 78 | CRDΔ1/2/3/4 | n/a |
| Mutant 1 (amino acid 21-193) | 79 | CRD1/2/3/4 | R7A/E8A |
| Mutant 2 (amino acid 21-193) | 80 | CRD1/2/3/4 | T32A/E33A |

TABLE 10-continued

CD40 ECD truncants and mutants

| CD40 ECD recombinant protein | SEQ ID NO. | CRD | Mutation |
|---|---|---|---|
| Mutant 3 (amino acid 21-193) | 81 | CRD1/2/3/4 | F34A/T35A |
| Mutant 4 (amino acid 21-193) | 82 | CRD1/2/3/4 | E35A/T37A |

Note:
CRD Δ 1: truncated CDR1 domain

Example 17 Humanized Anti-CD40 Antibodies Specifically Bound to Human CD40

ELISA assays were performed to determine the binding specificity of anti-CD40 antibodies to human CD40, in comparison to other human TNFR5F members with homologous amino acid sequences, following the protocol described in Example 2.

The binding affinities of anti-CD40 antibodies to human CD40 (ECD)-his (TNFRSF5, Sino Biological, China, Cat #:10774-H08H), human OX40-his (TNFR5F4, Sino Biological, China, Cat #:10481-H08H), human HVEM-mFc (TNFR5F14, ACRO, China, Cat #: HVM-H5255), human 4-1BB (TNFR5F9, ACRO, China, Cat #: 41B-H522a), human NGFR (TNFR5F16, Sino Biological, China, Cat #: 13184-H08H), human DR6 (TNFR5F21, Sino Biological, China, Cat #: 10175-H08H), human RANK(TNFR5F11, ACRO, China, Cat #: RAL-H5240) were studied.

Figure 15A:
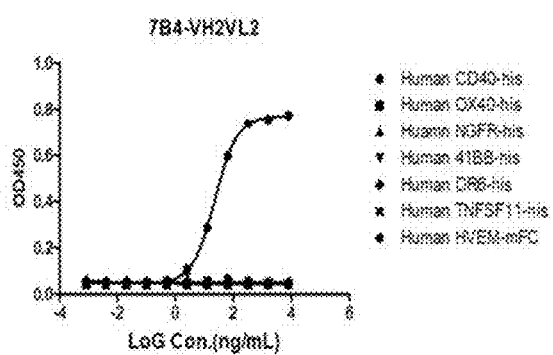
FIGS. 15A and 15B show the binding specificity of humanized anti-CD40 antibodies 7B4-VH2VL2 (A) and 13A2-VH3VL3 (B) to human CD40.
Figure 15B:
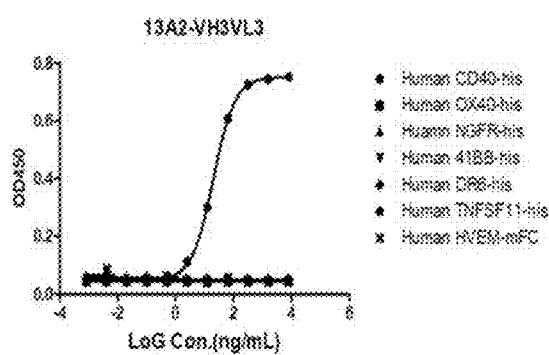
Figure 17A:
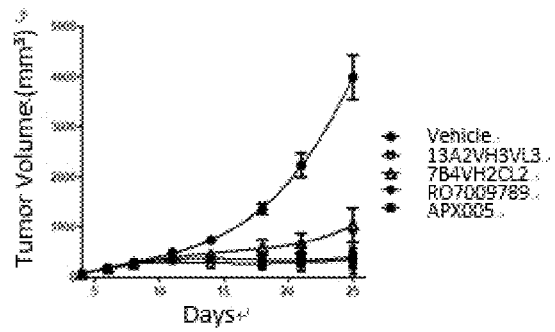
FIG. 17A-17F show the average tumor volume in each group (A) and individual tumor volumes in group administered with vehicle (B), 7B4VH2VL2 (C), 3A2VH3VL3 (D), RO7009789 (E) or APX005 (F).
Figure 17B:
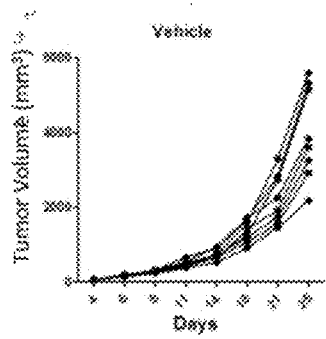
Figure 17C:
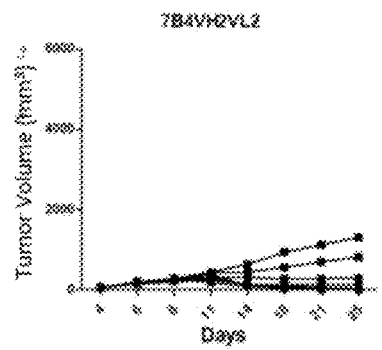
Figure 17D:
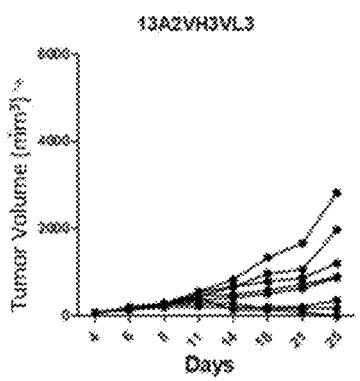
Figure 17E:
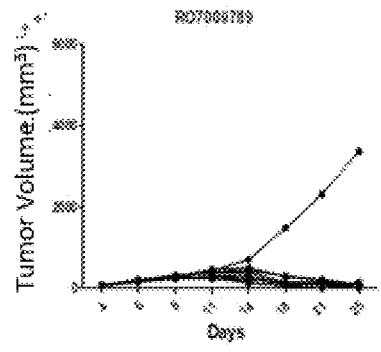
Figure 17F:
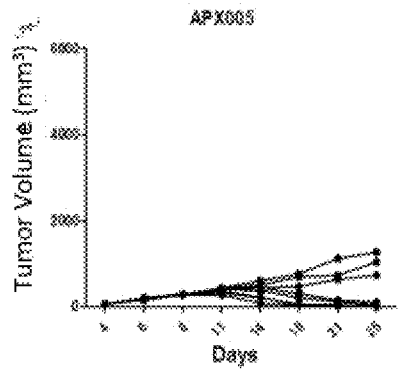

As shown in FIGS. 15A and 15B, neither 13A2VH3VL3 nor 7B4VH2VL2 showed binding to recombinant human OX40 (TNFR5F4), HVEM(TNFR5F14), 4-1BB (TNFR5F9), NGFR(TNFR5F16), DR6(TNFR5F21) or RANK(TNFR5F11), suggesting that 13A2VH3VL3 and 7B4VH2VL2 specifically bound to human CD40.

Example 18 Engineered Anti-CD40 Antibodies had Better Agonistic Activity

It has been suggested that optimal biological and anti-tumor effects of agonistic anti-CD40 antibodies require Fc receptor (FcR) coengagement (Richman and Vonderheide, (2014) *Cancer Immunol Res* 2(1): 19-26). Thus, anti-CD40 antibodies were prepared having heavy/light chain variable region of 13A2VH3VL3 or 7B4VH2VL2 plus human IgG1/kappa constant region, wherein the human IgG1 constant region was engineered to have S267E and L328F mutations (mutated IgG1 constant region's amino acid sequence set forth in SEQ ID NO.: 64). The obtained antibodies were named as 13A2-VH3VL3-IgG1(SE/LF) and 7B4-VH2VL2-IgG1(SE/LF), respectively, and were further characterized for their ability of promoting dendritic cell maturation, following the protocol in Example 9. RO7009789, ADC1013 and APX005 were used as positive controls, and Hel was used as negative control.

As shown in FIGS. 16A, 16B and 16C, 13A2-VH3VL3-IgG1(SE/LF) and 7B4-VH2VL2-IgG1(SE/LF) both showed significantly higher agonist activity in promoting dendritic cell maturation than their parents' antibodies, with 13A2-VH3VL3-IgG1(SE/LF) having the highest activity among all tested antibodies.

Example 19 Humanized Anti-CD40 Antibodies had In Vivo Anti-Tumor Effect

In vivo anti-tumor activity of anti-CD40 antibodies having heavy/light chain variable region of 13A2-VH3VL3 or 7B4-VH2VL2 and mouse IgG1/kappa constant regions (amino acid sequences of mouse IgG1/kappa constant regions set forth in SEQ ID NOs.: 62 and 66, respectively) were studied in an animal model established by grafting MC38 murine colon adenocarcinoma in transgenic mice with human CD40 (GemPharmatech Co. Ltd, China). Mouse IgG1/kappa constant regions were used to enhance Fc function in the mouse model. Each mouse was subcutaneously injected with $1\times10^6$ MC38 cells at one flank at day 0. When tumors grew to about 80 $mm^3$, the animals were randomly assigned into five groups, 8 mice per group. The animals were then i.p. administered with 13A2-VH3VL3, 7B4-VH2VL2, RO7009789, APX005 or PBS at a dose of 10 mg/kg/day at Day 4, 7, 11, 14, 18 and 21, RO7009789 and APX005 both engineered to have mouse IgG1/kappa constant regions (amino acid sequences of mouse IgG1/kappa constant regions set forth in SEQ ID NOs.: 62 and 66, respectively).

Tumor size and mice body weight were followed over time. Tumor measurements (width and length) were taken by caliper and tumor volume calculated by the formula TV=(length×width$^2$)/2. The experiment was terminated before the tumor volume in antibody administration groups reached 3.5 $cm^3$. One-way ANOVA was used to identify tumor volume differences.

At Day 25, four mice with bigger tumors from each group were selected for T cell analysis. The tumors were collected immediately after the mice were sacrificed and placed in Hanks buffer with collagenases. The tumors were then cut into small pieces and incubated in Hanks buffer with collagenases at 37° C. for 30 min with gentle shaking. Thereafter, 10 ml of RPMI 1640+10% FBS was added to each sample to deactivate the collagenase and maintain viability of the immune cells. Samples were passed through a 70 μm cell filter membrane (Corning, Cat #: 352350) and placed in new tubes. The samples were pelleted and resuspended in PBSF buffer (PBS+2% FBS) at a density of $1*10^7$ cells/ml. The samples were washed by PBSF buffer for 2 times. Each sample was divided into two parts, one added with anti-CD45 (Brilliant Violet 785™ anti-mouse CD45 Antibody; Biolegend; US; Cat #: 103149), anti-CD8 (APC anti-mouse CD8a Antibody; Biolegend; US; Cat #: 100712), anti-CD3 (FITC anti-mouse CD3 Antibody; Biolegend; US; Cat #: 100203) and anti-CD4 (PerCP anti-mouse CD4 Antibody; Biolegend; US; Cat #: 100432) fluorescent antibody mixtures, and another added with anti-CD11c (APC anti-mouse CD8a Antibody; Biolegend; US; Cat #: 100712), anti-CD80 (APC anti-mouse CD11c Antibody; Biolegend; US; Cat #: 117310), anti-CD83 (PE/Cy7 anti-mouse CD83 Antibody; Biolegend; US; Cat #: 121518) and anti-CD86 (FITC anti-mouse CD86 Antibody; Biolegend; US; Cat #: 105005) fluorescent antibody mixtures. The resultant mixtures were incubated for half an hour at 4° C. Cells were washed 2 times by PBSF buffer and analyzed on a FACS machine (BD).

As shown in FIG. 17A-17F, treatment with anti-CD40 antibodies significantly reduced or inhibited tumor growth, as compared to negative control group, although individuals responded differently. Tumor growth inhibition was observed in all mice (in the group with 7B4VH2VL2 or APX005 administration) or most mice (6 out of 8 in the group with 13A2VH3VL3 administration, 7 out of 8 in RO7009789 group). At Day 28, tumor vanished in all remaining 4 mice in 7B4VH2VL2 administration group while 2 out of 4 in APX005 administration group had no tumor at all.

Figure 18:
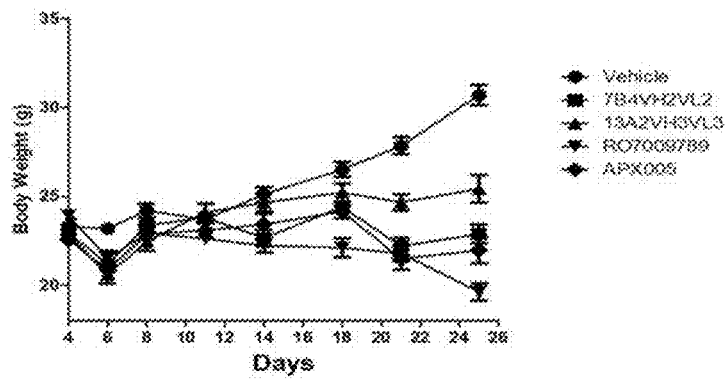
FIG. 18 shows the average animal body weight in group administered with humanized anti-CD40 antibodies of the invention or control agents.

Treatment with anti-CD40 antibodies may cause mice body weight reduction due to antibody's toxicity. As shown in FIG. 18 and Table 11 below, the body weights of mice in 13A2VH3VL3 group at Day 25 increased a bit compared to their initial weights, even if the tumor weights were taken into consideration (tumors at Day 25 were about 1000 $mm^3$ in size and 1.2 g in weight), indicating antibody 13A2VH3VL3's low toxicity. In other words, treatment with 13A2VH3VL3 did not cause significant body weight reduction as observed in the RO7009789 group, and had less effect on mice body weight than that in the 7B4VH2VL2 or APX005 group.

TABLE 11

| | Mice body weight (Mean ± SE (g), 8 mice per group) over time in five groups | | | | | | | |
|---|---|---|---|---|---|---|---|---|
| Group/Day | 4 | 6 | 8 | 11 | 14 | 18 | 21 | 25 |
| 13A2-VH3VL3 | 22.9 ± 0.5 | 20.6 ± 0.5 | 22.5 ± 0.5 | 24.1 ± 0.5 | 24.7 ± 0.5 | 25.2 ± 0.5 | 24.7 ± 0.5 | 25.4 ± 0.8 |
| 7B4-VH2VL2 | 23.0 ± 0.3 | 21.2 ± 0.2 | 23.4 ± 0.2 | 23.8 ± 0.2 | 22.7 ± 0.5 | 24.4 ± 0.2 | 22.2 ± 0.5 | 22.9 ± 0.5 |
| RO7009789 | 23.9 ± 0.3 | 21.5 ± 0.4 | 22.9 ± 0.4 | 22.6 ± 0.3 | 22.2 ± 0.4 | 22.1 ± 0.5 | 21.8 ± 0.4 | 19.6 ± 0.5 |
| APX005 | 22.6 ± 0.3 | 20.8 ± 0.3 | 22.9 ± 0.3 | 23.1 ± 0.4 | 23.4 ± 0.6 | 24.1 ± 0.4 | 21.5 ± 0.6 | 22.0 ± 0.7 |
| PBS | 23.3 ± 0.4 | 23.2 ± 0.3 | 24.2 ± 0.4 | 23.7 ± 0.3 | 25.1 ± 0.4 | 26.5 ± 0.4 | 27.8 ± 0.5 | 30.7 ± 0.6 |

FIGS. 19A and 19B showed that antibody 7B4VH2VL2 evidently elevated percentage of both $CD45^+$ $CD3^+$ $CD8^+$ cells and $CD45^+$ $CD3^+$ $CD4^+$ cell in $CD45^+$ cells. The percentage of $CD45^+$ $CD3^+$ $CD8^+$ cells was also increased in 13A2VH3VL3 treated mice. In addition, FIG. 20 indicated 7B4VH2VL2 treatment significantly increased CD80 and CD83 expression on tumor infiltrating dendritic cells ($CD45^+$ $CD11c^+$ cells), indicating its strong agonist activity in promoting dendritic cells maturation.

Amino acid sequences of some antibodies' heavy/light chain variable regions were summarized below.

| Description/Sequence/SEQ ID NO. |
|---|
| VH for mouse, and chimeric 92F6 antibodies (CDR regions underlined and bold) |
| QVQLEQSGAEVVKPGASVKVSCTASGFNIKDTYMHWVKQRPEQGLEWIGR IDPANGNTNYDPKFQGKATITADTSSNTGYLQLSSLTSEDTAVYYCSRWG YDWYFDVWGAGTSVTVSS (SEQ ID NO: 41) |
| VL for mouse, and chimeric 92F6 antibodies (CDR regions underlined and bold) |
| DIVITQSTAIMSASPGEKVTITCSASSSVSYIHWFQQKPGTSPKLWIYTT ANLASGVPARFSGSGSGTSYSLTISRMEAEDAATYYCQQRSNYPFTFGSG TKLEIK (SEQ ID NO: 55) |

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

We claim:

1. An isolated monoclonal antibody, or an antigen-binding portion thereof, binding to tumor necrosis factor receptor CD40, comprising a heavy chain variable region comprising a VH-CDR1 region, a VH-CDR2 region and a VH-CDR3 region, and a light chain variable region comprising a VL-CDR1 region, a VL-CDR2 region and a VL-CDR3 region, wherein the VH-CDR1 region, VH-CDR2 region, VH-CDR3 region and the VL-CDR1 region, VL-CDR2 region and VL-CDR3 region comprise amino acid sequences of SEQ ID NOs: 4, 11, 17, 23, 29 and 33, respectively.

2. The isolated monoclonal antibody, or the antigen-binding portion thereof, of claim 1, wherein the heavy chain variable region comprises an amino acid sequence set forth in SEQ ID NO: 41.

3. The isolated monoclonal antibody, or the antigen-binding portion thereof, of claim 1, wherein the light chain variable region comprises an amino acid sequence set forth in SEQ ID NO: 55.

4. The isolated monoclonal antibody, or the antigen-binding portion thereof, of claim 1, wherein the heavy chain variable region and the light chain variable region comprise amino acid sequences set forth in SEQ ID NOs: 41 and 55, respectively.

5. The isolated monoclonal antibody, or the antigen-binding portion thereof, of claim 1, comprising a heavy chain constant region having an amino acid sequence set forth in SEQ ID NOs: 62, 63 or 64, linked to the heavy chain variable region, and a light chain constant region having an amino acid sequence set forth in SEQ ID NOs: 65 or 66, linked to the light chain variable region.

6. The isolated monoclonal antibody, or the antigen-binding portion thereof, of claim 1, which (a) binds CD40, (b) binds monkey CD40; (c) does not bind to mouse CD40; (d) blocks CD40-CD40L interaction and (e) activates CD40 signaling; and (f) promotes DC cell maturation.

7. The isolated monoclonal antibody, or the antigen-binding portion thereof, of claim 1, which is a mouse, or chimeric antibody.

8. The isolated monoclonal antibody, or the antigen-binding portion thereof, of claim 1, which is an IgG1, IgG2 or IgG4 isotype.

9. A pharmaceutical composition comprising the isolated monoclonal antibody, or the antigen-binding portion thereof, of claim 1, and a pharmaceutically acceptable carrier.

10. A method for activating or inducing CD40 signaling to promote immune cell activation or proliferation in a subject having cancer, comprising administering to the subject a therapeutically effective amount of the pharmaceutical composition of claim 9.

11. The method of claim 10, wherein the cancer is a solid or non-solid tumor.

12. The method of claim 10, wherein the cancer is selected from the group consisting of B cell lymphoma, chronic lymphocytic leukemia, multiple myeloma, melanoma, colon adenocarcinoma, pancreas cancer, colon cancer, gastric intestine cancer, prostate cancer, bladder cancer, kidney cancer, ovary cancer, cervix cancer, breast cancer, lung cancer, and nasopharynx cancer.

13. The method of claim 10, further comprising administering an immunostimulatory antibody, a costimulatory antibody, a chemotherapeutic agent, and/or a cytokine.

14. The method of claim 13, wherein the immunostimulatory antibody is selected from the group consisting of an anti-VISTA antibody, an anti-PD-1 antibody, an anti-PD-L1 antibody, an anti-LAG-3 antibody, an anti-TIM 3 antibody, an anti-STAT3 antibody, and an anti-ROR1 antibody.

15. The method of claim 13, wherein the costimulatory antibody is an anti-CD137 antibody or an anti-GITR antibody.

16. The method of claim 13, wherein the chemotherapeutic agent is epitubicin, oxaliplatin, and/or 5-fluorouracil.

17. The method of claim 13, wherein the cytokine is GM-CSF and/or IL-4.

* * * * *